(12) United States Patent
Tang et al.

(10) Patent No.: US 8,921,573 B2
(45) Date of Patent: Dec. 30, 2014

(54) PROCESSES FOR THE PREPARATION OF NOVEL BENZIMIDAZOLE DERIVATIVES

(71) Applicant: Enanta Pharmaceuticals, Inc., Watertown, MA (US)

(72) Inventors: Datong Tang, Newton, MA (US); Guoyou Xu, Framingham, MA (US); Xiaowen Peng, Cambridge, MA (US); Lu Ying, Shanghai (CN); Ce Wang, Beijing (CN); Hui Cao, Belmont, MA (US); Jiang Long, Wayland, MA (US); In Jong Kim, Lexington, MA (US); Guoqiang Wang, Belmont, MA (US); Yao-Ling Qiu, Andover, MA (US); Yat Sun Or, Watertown, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 14/253,976

(22) Filed: Apr. 16, 2014

(65) Prior Publication Data
US 2014/0316143 A1  Oct. 23, 2014

Related U.S. Application Data

(63) Continuation of application No. PCT/US2012/060560, filed on Oct. 17, 2012.

(60) Provisional application No. 61/548,374, filed on Oct. 18, 2011.

(51) Int. Cl.
C07D 403/14   (2006.01)

(52) U.S. Cl.
CPC .................................. *C07D 403/14* (2013.01)
USPC ....................................................... 548/300.7

(58) Field of Classification Search
USPC ....................................................... 548/300.7
See application file for complete search history.

(56) References Cited

U.S. PATENT DOCUMENTS

2010/0215616 A1* 8/2010 Romine et al. ............... 424/85.2

* cited by examiner

*Primary Examiner* — Laura L. Stockton
(74) *Attorney, Agent, or Firm* — Roy P. Issac; Carolyn S. Elmore, Esq.; Elmore Patent Law Group P.C.

(57) ABSTRACT

The present invention relates to processes and intermediates for the preparation of novel benzimidazole derivatives, especially in the synthesis of hepatitis C virus NS5A inhibitors. In particular, the present invention relates to processes and intermediates for the preparation of compounds of formulae (I-a):

(I-a)

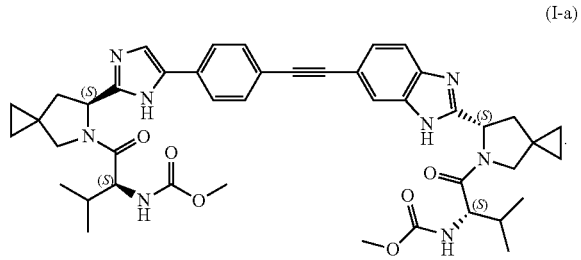

15 Claims, No Drawings

PROCESSES FOR THE PREPARATION OF NOVEL BENZIMIDAZOLE DERIVATIVES

RELATED APPLICATION(S)

This application is a continuation of International Application No. PCT/US2012/60560, which designated the United States and was filed on Oct. 17, 2012, published in English, which claims the benefit of U.S. Provisional Application No. 61/548,374, filed on Oct. 18, 2011. The entire teachings of the above applications are incorporated herein by reference.

TECHNICAL FIELD

The present invention relates to processes and intermediates useful in the preparation of biologically active molecules, especially in the synthesis of hepatits C virus NS5A inhibitors.

BACKGROUND OF THE INVENTION

Infection with HCV is a major cause of human liver disease throughout the world. In the US, an estimated 4.5 million Americans are chronically infected with HCV. Worldwide over 200 million people are estimated to be infected chronically. Due to the high degree of variability in the viral surface antigens, existence of multiple viral genotypes, and demonstrated specificity of immunity, the development of a successful vaccine in the near future is unlikely. There are several non-structural proteins. NS5A is a membrane-anchored phosphoprotein that is observed in basally phosphorylated (56 kDa) and hyperphosphorylated (58 kDa) forms. While its function has not fully been elucidated, NS5A is believed to be important in viral replication. Compounds useful for treating HCV-infected patients are desired which selectively inhibit HCV viral replication. In particular, compounds which are effective to inhibit the function of the NS5A protein are desired. The HCV NS5A protein is described, for example, in Tan, S.-L., Katzel, M. G. *Virology* 2001, 284, 1; and in Rice, C. M. *Nature* 2005, 435, 374.

SUMMARY OF THE INVENTION

The present invention provides methods for preparing compounds of Formula (I):

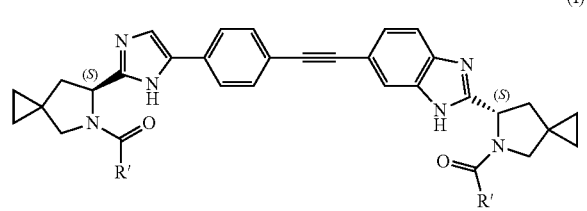

wherein each R' is independently selected from substituted $C_1$-$C_8$ alkyl groups or a pharmaceutically acceptable salt thereof. Preferably, each R' is independently $C_1$-$C_8$ alkyl substituted with —NHCO$_2$($C_1$-$C_4$ alkyl) or —O($C_1$-$C_4$ alkyl); or a pharmaceutically acceptable salt thereof.

A preferred embodiment of a compound of Formula (I) is the compound of Formula (I-a):

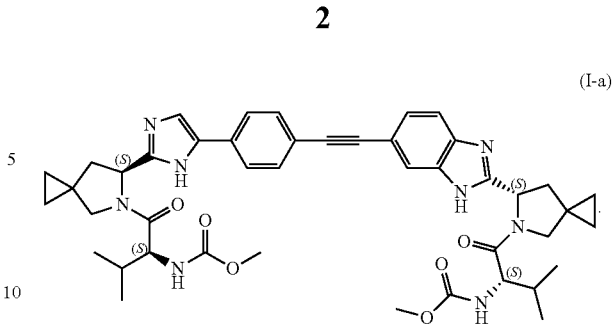

The invention relates to a method of preparing a spirocyclopropane compound of Formula (VIII), as defined below, comprising the step of (a) treating a sulfur glide with an exocyclic α,β-unsaturated ketone to give a spirocyclopropane intermediate, (b) reducing the spirocyclopropane intermediate of step (a), (c) protecting group manipulation and (d) oxidation.

The invention further relates to methods for increasing product yield and decreasing process steps for intermediate and large scale production of compounds of Formula (I or I-a). These compounds are useful as hepatitis C virus NS5A inhibitors (WO2010/099527A1).

DETAILED DESCRIPTION OF THE INVENTION

In its principal embodiment, the present invention provides a process for the preparation of compounds of Formula (I):

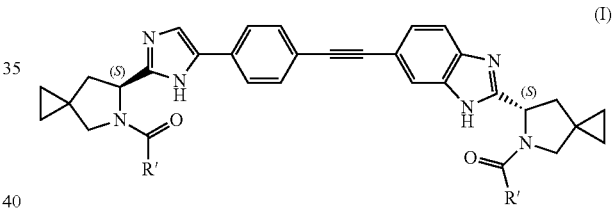

wherein R' is a substituted $C_1$-$C_8$ alkyl group, or a pharmaceutically acceptable salt thereof. Preferably, R' is $C_1$-$C_8$ alkyl substituted with —NHCO$_2$($C_1$-$C_4$ alkyl) or —O($C_1$-$C_4$ alkyl); or a pharmaceutically acceptable salt thereof the process comprising:
(a) providing a compound of Formula (III):

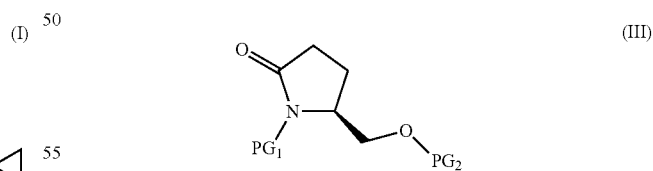

wherein PG$_1$ is selected from the group consisting of —C(O)—R, —C(O)—OR, —S(O)$_2$—R, —C(O)N(R)$_2$, and —S(O)$_2$N(R)$_2$;

R is selected from the group consisting of hydrogen, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkenyl, heterocyclic, aryl, and heteroaryl, each optionally substituted;

PG$_2$ is selected from acyl, silyl, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, a saturated or unsaturated heterocyclic group;

alternatively, $PG_1$ and $PG_2$ are tethered together to form a compound of Formula (III-a):

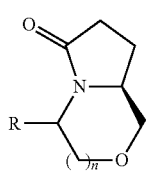
(III-a)

wherein R is as previously defined and n is 0, 1, or 2.

In a most preferred embodiment, the compound of Formula (III) is a compound of Formula (III-b):

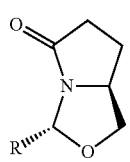
(III-b)

(b) treating the compound of Formula (III) with a deprotonating agent followed by an alkylating agent followed by a quaternizing agent to provide a compound of Formula (IV):

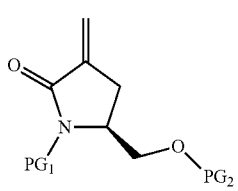
(IV)

Preferred embodiments of the compound of Formula (IV) are compounds of formulas (IV-a) and (IV-b):

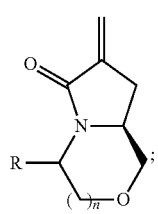
(IV-a)

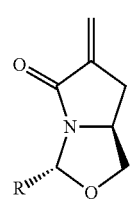
(IV-b)

(c) reacting the compound of Formula (IV) with a sulfur glide in the presence of a base to yield a compound of Formula (V):

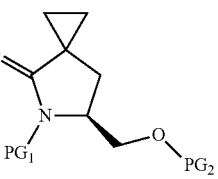
(V)

Preferred embodiments of the compound of Formula (V) are compounds of formulas (V-a) and (V-b):

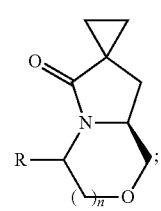
(V-a)

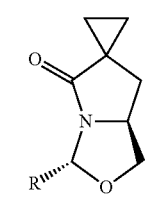
(V-b)

(d) reducing and deprotecting the compound of Formula (V) to provide a compound of Formula (VI):

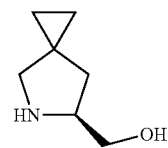
(VI)

(e) protecting the compound of Formula (VI) to yield a compound of Formula (VII):

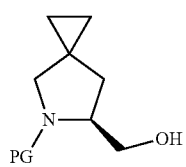
(VII)

wherein PG is selected from the group consisting of —R, —C(O)—R, —C(O)—OR, —S(O)$_2$—R, —C(O)N(R)$_2$, and —S(O)$_2$N(R)$_2$, wherein R is as previously defined; preferably, PG is Boc or Cbz;

(f) reacting the compound of Formula (VII) with an oxidizing reagent to yield a compound of Formula (VIII):

(VIII)

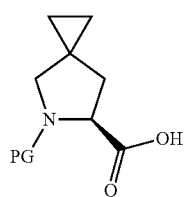

(g) reacting the compound of Formula (IX):

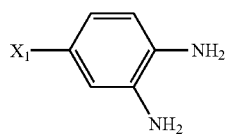

wherein $X_1$ is a leaving group, with $R_1$—≡—H, wherein $R_1$ is hydrogen or silyl, in the presence of a metallic catalyst to provide a compound of Formula (X):

(X)

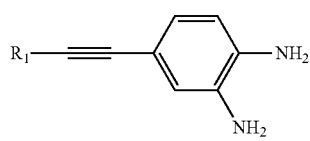

(h) reacting the compound of Formula (VIII) with the compound of Formula (X) in the presence of an amide coupling agent to provide a mixture of compounds of Formulae (XI-a) and (XI-b):

(XI-a)

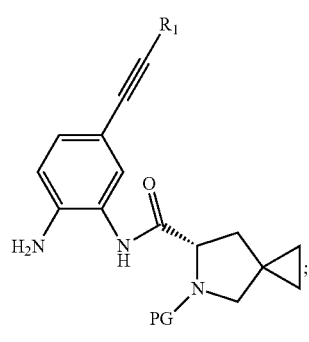

(XI-b)

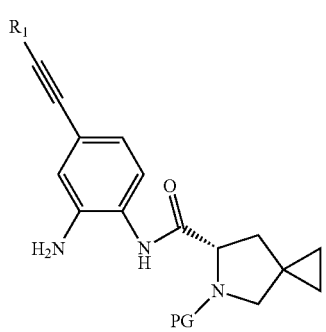

(i) treating the mixture of compounds of Formulae (XI-a) and (XI-b) with an acid to yield a compound of Formula (XII):

(XII)

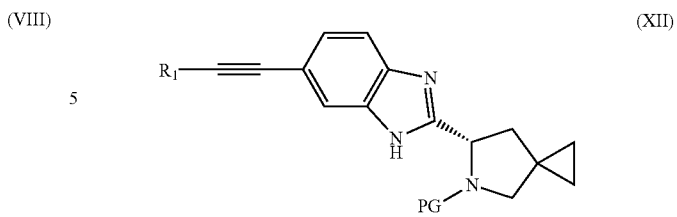

(j) if $R_1$ is a silyl group, treating the compound of Formula (XII) with a base to yield a compound of Formula (XII-a):

(XII-a)

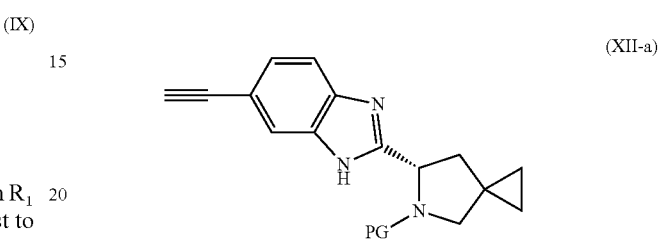

(k) treating a compound of Formula (XIII)

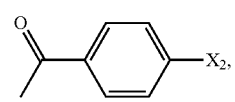

wherein $X_2$ is a leaving group, with a halogenating reagent to yield a compound of Formula (XIV):

(XIV)

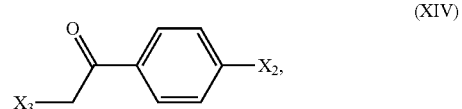

wherein $X_3$ is halogen (l) reacting the compound of Formula (VIII) with the compound of Formula (XIV) in the presence of a base to provide a compound of Formula (XV):

(XV)

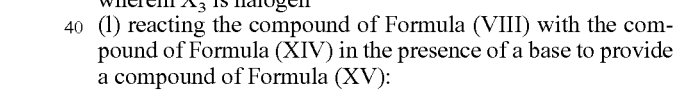

(m) treating the compound of formula (XV) with an ammonium salt to provide a compound of Formula (XVI):

(XVI)

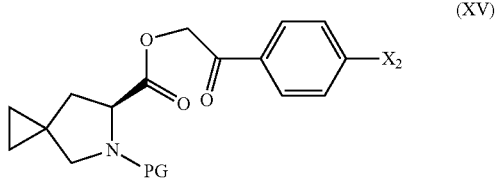

(n) reacting the compound of Formula (XII-a) with the compound of Formula (XVI) in the presence of a metallic catalyst to provide a compound of Formula (XVII):

(XVII)

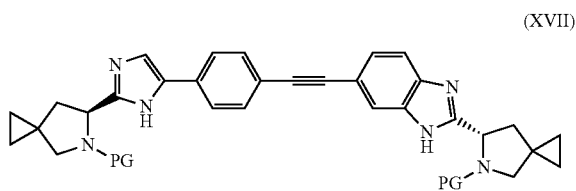

(o) deprotecting the compound of Formula (XVII) to provide a compound of Formula (XVIII):

(XVIII)

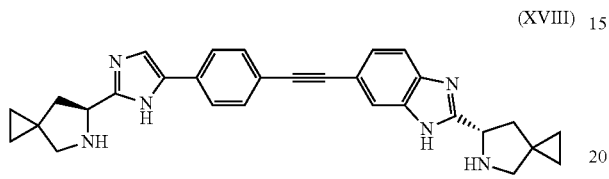

(p) reacting the compound of Formula (XVIII) with

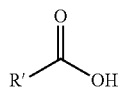

in the presence of an amide coupling reagent to provide a compound of Formula (I):

(I)

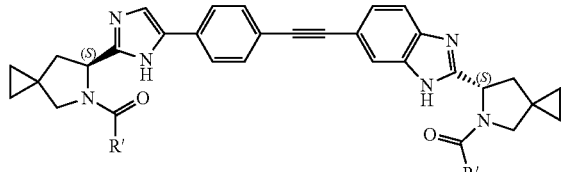

wherein R' is selected from substituted $C_1$-$C_8$ alkyl groups or a pharmaceutically acceptable salt thereof. Preferably, R' is $C_1$-$C_8$ alkyl substituted with —$NHCO_2$($C_1$-$C_4$ alkyl) or —O($C_1$-$C_4$ alkyl); or a pharmaceutically acceptable salt thereof.

In one embodiment, the compound of Formula III is prepared by protecting a compound of Formula II, (II)

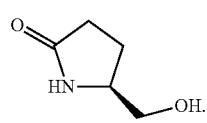

In yet another embodiment of the invention a compound of formula (XII) is prepared by the process comprising the steps of:

(a) reacting the compound of Formula (VIII) with the compound of Formula (IX) in the presence of an amide coupling reagent to provide a mixture of compounds of Formulae (XIV-a) and (XIV-b), where $X_1$ is as previously defined:

(XIV-b)

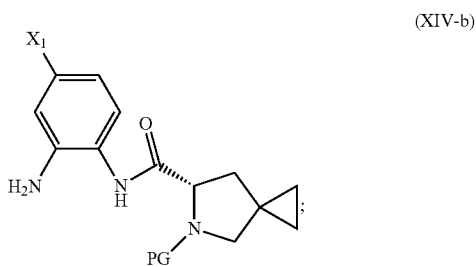

(XIV-a)

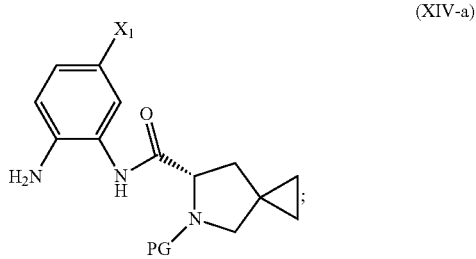

(b) treating the mixture of compounds of Formulas (XIV) with an acid to yield a compound of Formula (XX):

(XX)

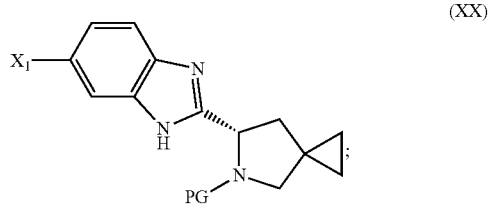

(c) reacting the compound of Formula (XX) with $R_1$—≡—H, wherein $R_1$ is hydrogen or silyl, in the presence of a metallic catalyst to provide the compound of Formula (XII):

(XII)

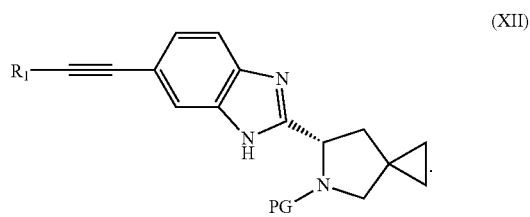

In yet another embodiment of the invention a compound of formula (XVII) is prepared by a process comprising the steps of:

(a) reacting the compound of Formula (XVI) with $R_1$—≡—H, wherein $R_1$ is hydrogen or silyl, in the presence of a metallic catalyst to provide a compound of Formula (XXI):

(XXI)

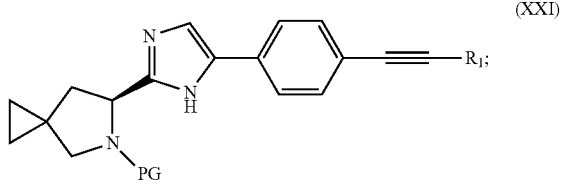

and (b) reacting the compound of Formula (XXI) with the compound of Formula (XX) in the presence of a metallic catalyst to provide the compound of Formula (XVII):

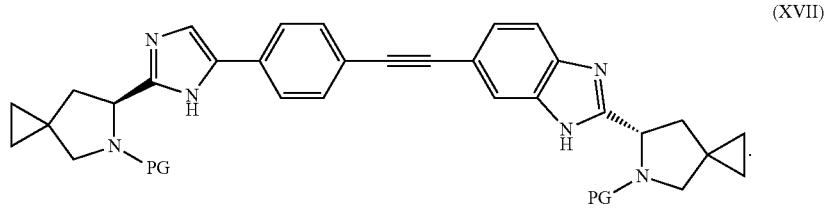

(XVII)

DEFINITIONS

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono- or polycyclic carbocyclic ring system comprising at least one aromatic ring, including, but not limited to, phenyl, naphthyl, tetrahydronaphthyl, indanyl, idenyl. A polycyclic aryl is a polycyclic ring system that comprises at least one aromatic ring. Polycyclic aryls can comprise fused rings, covalently attached rings or a combination thereof.

The term "heteroaryl," as used herein, refers to a mono- or polycyclic aromatic radical having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl. A polycyclic heteroaryl can comprise fused rings, covalently attached rings or a combination thereof.

In accordance with the invention, aromatic groups can be substituted or unsubstituted.

The terms "$C_1$-$C_4$ alkyl," "$C_1$-$C_6$ alkyl," or "$C_1$-$C_8$ alkyl," as used herein, refer to saturated, straight- or branched-chain hydrocarbon radicals containing between one and four, one and six, one and eight carbon atoms, respectively. Examples of $C_1$-$C_8$ alkyl radicals include, but are not limited to, methyl, ethyl, propyl, isopropyl, n-butyl, tert-butyl, neopentyl, n-hexyl, heptyl and octyl radicals.

The terms "$C_2$-$C_8$ alkenyl," or "$C_2$-$C_4$ alkenyl," as used herein, refer to straight- or branched-chain hydrocarbon radicals containing from two to eight, or two to four carbon atoms, having at least one carbon-carbon double bond by the removal of a single hydrogen atom. Alkenyl groups include, but are not limited to, for example, ethenyl, propenyl, butenyl, 1-methyl-2-buten-1-yl, heptenyl, octenyl, and the like.

The terms "$C_2$-$C_8$ alkynyl," or "$C_2$-$C_4$ alkynyl," as used herein, refer to straight- or branched-chain hydrocarbon radicals containing from two to eight, or two to four carbon atoms, having at least one carbon-carbon triple bond by the removal of a single hydrogen atom. Representative alkynyl groups include, but are not limited to, for example, ethynyl, 1-propynyl, 1-butynyl, heptynyl, octynyl, and the like.

The term "$C_3$-$C_8$ cycloalkyl", as used herein, refers to a monocyclic or polycyclic saturated carbocyclic ring compound, and the carbon atoms may be optionally oxo-substituted. Examples of $C_3$-$C_8$ cycloalkyl include, but not limited to, cyclopropyl, cyclobutyl, cyclopentyl, cyclohexyl, cyclopentyl and cyclooctyl; and examples of $C_4$-$C_7$ cycloalkyl include, but not limited to, cyclopentyl, cyclohexyl, bicyclo [2.2.1] heptyl, and the like.

The term "$C_3$-$C_8$ cycloalkenyl", as used herein, refers to monocyclic or polycyclic carbocyclic ring compound having at least one carbon-carbon double bond and the carbon atoms may be optionally oxo-substituted. Examples of $C_3$-$C_8$ cycloalkenyl include, but not limited to, cyclopropenyl, cyclobutenyl, cyclopentenyl, cyclohexenyl, cycloheptenyl, cyclooctenyl, and the like; and examples of $C_5$-$C_7$ cycloalkenyl include, but not limited to, cyclopentenyl, cyclohexenyl, cycloheptenyl, and the like.

It is understood that any alkyl, alkenyl, alkynyl, cycloalkyl, heterocyclic and cycloalkenyl moiety described herein can also be an aliphatic group or an alicyclic group.

An "aliphatic" group is a non-aromatic moiety comprised of any combination of carbon atoms, hydrogen atoms, halogen atoms, oxygen, nitrogen or other atoms, and optionally contains one or more units of unsaturation, e.g., double and/or triple bonds. Examples of aliphatic groups are functional groups, such as, O, OH, NH, $NH_2$, C(O), $S(O)_2$, C(O)O, C(O)NH, OC(O)O, OC(O)NH, $OC(O)NH_2$, $S(O)_2NH$, $S(O)_2NH_2$, $NHC(O)NH_2$, NHC(O)C(O)NH, $NHS(O)_2NH$, $NHS(O)_2NH_2$, $C(O)NHS(O)_2$, $C(O)NHS(O)_2NH$ or $C(O)NHS(O)_2NH_2$, and the like, groups comprising one or more functional groups, non-aromatic hydrocarbons (optionally substituted), and groups wherein one or more carbons of a non-aromatic hydrocarbon (optionally substituted) is replaced by a functional group. Carbon atoms of an aliphatic group can be optionally oxo-substituted. An aliphatic group may be straight chained, branched, cyclic, or a combination thereof and preferably contains between about 1 and about 24 carbon atoms, more typically between about 1 and about 12 carbon atoms. In addition to aliphatic hydrocarbon groups, as used herein, aliphatic groups expressly include, for example, alkoxyalkyls, polyalkoxyalkyls, such as polyalkylene glycols, polyamines, and polyimines, for example. Aliphatic groups may be optionally substituted. A linear aliphatic group is a non-cyclic aliphatic group. It is to be understood that when an aliphatic group or a linear aliphatic group is said to "contain" or "include" or "comprise" one or more specified functional groups, the linear aliphatic group can be selected from one or more of the specified functional groups or a combination thereof, or a group wherein one or more carbons of a non-aromatic hydrocarbon (optionally substituted) is replaced by a specified functional group. In another aspect of the invention, an exemplary linear aliphatic group is an alkyl, alkenyl or alkynyl, each optionally substituted, which is interrupted or terminated by a functional group such as described herein.

The term "alicyclic," as used herein, denotes a monovalent group derived from a monocyclic or bicyclic saturated carbocyclic ring compound by the removal of a single hydrogen atom, and the carbon atoms may be optionally oxo-substituted. Examples include, but not limited to, cyclopropyl, cyclobutyl, cyclopentyl, cyclohexyl, bicyclo [2.2.1] heptyl, and bicyclo[2.2.2] octyl. Such alicyclic groups may be further substituted.

The terms "heterocyclic" or "heterocycloalkyl" can be used interchangeably and referred to a non-aromatic ring or a bi- or tri-cyclic group fused system, where: (i) each ring system contains at least one heteroatom independently selected from oxygen, sulfur and nitrogen, (ii) each ring system can be saturated or unsaturated, (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl. Such heterocyclic groups may be further substituted. Heteroaryl or heterocyclic groups can be C-attached or N-attached (where possible).

It is understood that any alkyl, alkenyl, alkynyl, alicyclic, cycloalkyl, cycloalkenyl, aryl, heteroaryl, heterocyclic, aliphatic moiety or the like, described herein can also be a divalent or multivalent group when used as a linkage to connect two or more groups or substituents, which can be at the same or different atom(s).

The term "acyl" refers to a residue derived from an organic acid, such as, but not limited to a carboxylic acid, a carbamic acid, a carbonic acid, a sulfonic acid, or a phosphonic acid. Examples include aliphatic carbonyls, aromatic carbonyls, aliphatic sulfonyls, aromatic sulfinyls, aliphatic sulfinyls, aromatic phosphates and aliphatic phosphates. Examples of aliphatic carbonyls include, but are not limited to, formyl, acetyl, propionyl, 2-fluoroacetyl, butyryl, 2-hydroxyacetyl, and the like.

The term "silyl" refers to a residue derived from a silane, such as a trialkyl silane or an aryldialkylsilane, by removal of a hydrogen atom. Examples of silyl groups include trimethylsilyl, triisopropylsilyl, triethylsilyl, t-butyldimethylsilyl, biphenyldimethylsilyl, and biphenyldiisopropylsilyl. A preferred silyl group is trimethylsilyl.

The term "substituted" refers to substitution by independent replacement of one, two, or three or more of the hydrogen atoms with substituents including, but not limited to, —F, —Cl, —Br, —I, —OH, protected hydroxy, —NO$_2$, —N$_3$, —CN, —NH$_2$, protected amino, oxo, thioxo, —NH—C$_1$-C$_{12}$-alkyl, —NH—C$_2$-C$_8$-alkenyl, —NH—C$_2$-C$_8$-alkynyl, —NH—C$_3$-C$_{12}$-cycloalkyl, —NH-aryl, —NH-heteroaryl, —NH-heterocycloalkyl, -dialkylamino, -diarylamino, -diheteroarylamino, —O—C$_1$-C$_{12}$-alkyl, —O—C$_2$-C$_8$-alkenyl, —O—C$_2$-C$_8$-alkynyl, —O—C$_3$-C$_{12}$-cycloalkyl, —O-aryl, —O-heteroaryl, —O-heterocycloalkyl, —C(O)—C$_1$-C$_{12}$-alkyl, —C(O)—C$_2$-C$_8$-alkenyl, —C(O)—C$_2$-C$_8$-alkynyl, —C(O)—C$_3$-C$_{12}$-cycloalkyl, —C(O)-aryl, —C(O)-heteroaryl, —C(O)-heterocycloalkyl, —CONH$_2$, —CONH—C$_1$-C$_{12}$-alkyl, —CONH—C$_2$-C$_8$-alkenyl, —CONH—C$_2$-C$_8$-alkynyl, —CONH—C$_3$-C$_{12}$-cycloalkyl, —CONH-aryl, —CONH-heteroaryl, —CONH-heterocycloalkyl, —OCO$_2$—C$_1$-C$_{12}$-alkyl, —OCO$_2$—C$_2$-C$_8$-alkenyl, —OCO$_2$—C$_2$-C$_8$-alkenyl, —OCO$_2$—C$_3$-C$_{12}$-cycloalkyl, —OCO$_2$-aryl, —OCO$_2$-heteroaryl, —OCO$_2$-heterocycloalkyl, —CO$_2$—C$_1$-C$_{12}$ alkyl, —CO$_2$—C$_2$-C$_8$ alkenyl, —CO$_2$—C$_2$-C$_8$ alkynyl, CO$_2$—C$_3$-C$_{12}$-cycloalkyl, —CO$_2$-aryl, CO$_2$-heteroaryl, CO$_2$-heterocyloalkyl, —OCONH$_2$, —OCONH—C$_1$-C$_{12}$-alkyl, —OCONH—C$_2$-C$_8$-alkenyl, —OCONH—C$_2$-C$_8$-alkynyl, —OCONH—C$_3$-C$_{12}$-cycloalkyl, —OCONH-aryl, —OCONH-heteroaryl, —OCONH-heterocyclo-alkyl, —NHC(O)H, —NHC(O)—C$_1$-C$_{12}$-alkyl, —NHC(O)—C$_2$-C$_8$-alkenyl, —NHC(O)—C$_2$-C$_8$-alkynyl, —NHC(O)—C$_3$-C$_{12}$-cycloalkyl, —NHC(O)-aryl, —NHC(O)-heteroaryl, —NHC(O)-heterocycloalkyl, —NHCO$_2$—C$_1$-C$_{12}$-alkyl, —NHCO$_2$—C$_2$-C$_8$-alkenyl, —NHCO$_2$—C$_2$-C$_8$-alkynyl, —NHCO$_2$—C$_3$-C$_{12}$-cycloalkyl, —NHCO$_2$-aryl, —NHCO$_2$-heteroaryl, —NHCO$_2$-heterocycloalkyl, —NHC(O)NH$_2$, —NHC(O)NH—C$_1$-C$_{12}$-alkyl, —NHC(O)NH—C$_2$-C$_8$-alkenyl, —NHC(O)NH—C$_2$-C$_8$-alkynyl, —NHC(O)NH—C$_3$-C$_{12}$-cycloalkyl, —NHC(O)NH-aryl, —NHC(O)NH-heteroaryl, —NHC(O)NH-heterocycloalkyl, NHC(S)NH$_2$, —NHC(S)NH—C$_1$-C$_{12}$-alkyl, —NHC(S)NH—C$_2$-C$_8$-alkenyl, —NHC(S)NH—C$_2$-C$_8$-alkynyl, —NHC(S)NH—C$_3$-C$_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH—C$_1$-C$_{12}$-alkyl, —NHC(NH)NH—C$_2$-C$_8$-alkenyl, —NHC(NH)NH—C$_2$-C$_8$-alkynyl, —NHC(NH)NH—C$_3$-C$_{12}$-cycloalkyl, —NHC(NH)NH-aryl, —NHC(NH)NH-heteroaryl, —NHC(NH)NH-heterocycloalkyl, —NHC(NH)—C$_1$-C$_{12}$-alkyl, —NHC(NH)—C$_2$-C$_8$-alkenyl, —NHC(NH)—C$_2$-C$_8$-alkynyl, —NHC(NH)—C$_3$-C$_{12}$-cycloalkyl, —NHC(NH)-aryl, —NHC(NH)-heteroaryl, —NHC(NH)-heterocycloalkyl, —C(NH)NH—C$_1$-C$_{12}$-alkyl, —C(NH)NH—C$_2$-C$_8$-alkenyl, —C(NH)NH—C$_2$-C$_8$-alkynyl, —C(NH)NH—C$_3$-C$_{12}$-cycloalkyl, —C(NH)NH-aryl, —C(NH)NH-heteroaryl, —C(NH)NH-heterocycloalkyl, —S(O)—C$_1$-C$_{12}$-alkyl, —S(O)—C$_2$-C$_8$-alkenyl, —S(O)—C$_2$-C$_8$-alkynyl, —S(O)—C$_3$-C$_{12}$-cycloalkyl, —S(O)-aryl, —S(O)-heteroaryl, —S(O)-heterocycloalkyl, —SO$_2$NH$_2$, —SO$_2$NH—C$_1$-C$_{12}$-alkyl, —SO$_2$NH—C$_2$-C$_8$-alkenyl, —SO$_2$NH—C$_2$-C$_8$-alkynyl, —SO$_2$NH—C$_3$-C$_{12}$-cycloalkyl, —SO$_2$NH-aryl, —SO$_2$NH-heteroaryl, —SO$_2$NH-heterocycloalkyl, —NHSO$_2$—C$_1$-C$_{12}$-alkyl, —NHSO$_2$—C$_2$-C$_8$-alkenyl, —NHSO$_2$—C$_2$-C$_8$-alkynyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_8$-alkenyl, —S—C$_2$-C$_8$-alkynyl, —S—C$_3$-C$_{12}$-cycloalkyl, —S-aryl, —S-heteroaryl, —S-heterocycloalkyl, or methylthio-methyl. It is understood that the aryls, heteroaryls, alkyls, and the like can be further substituted.

The term "halogen," as used herein, refers to an atom selected from fluorine, chlorine, bromine and iodine.

The term "hydrogen" includes hydrogen and deuterium. In addition, the recitation of an atom includes other isotopes of that atom so long as the resulting compound is pharmaceutically acceptable.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995).

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Suitable concentrations of reactants used in the synthesis processes of the invention are 0.01M to 10M, typically 0.1M to 1M. Suitable temperatures include −10° C. to 250° C., typically −78° C. to 150° C., more typically −78° C. to 100° C., still more typically 0° C. to 100° C. Reaction vessels are preferably made of any material which does not substantial interfere with the reaction. Examples include glass, plastic, and metal. The pressure of the reaction can advantageously be operated at atmospheric pressure. The atmospheres include, for example, air, for oxygen and water insensitive reactions, or nitrogen or argon, for oxygen or water sensitive reactions.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, triflate brosylate, nosylate and the like; and acyloxy groups, such as acetoxy, trifluoroacetoxy and the like.

The term "in situ," as used herein, refers to use of an intermediate in the solvent or solvents in which the intermediate was prepared without removal of the solvent.

ABBREVIATIONS

Abbreviations which may be used in the descriptions of the scheme and the examples that follow are: Ac for acetyl; AcOH for acetic acid; AIBN for azobisisobutyronitrile; Boc$_2$O for di-tert-butyl-dicarbonate; Boc for t-butoxycarbonyl; BPO for benzoyl peroxide; Bz for benzoyl; Bn for benzyl; t-BuOK for potassium tert-butoxide; Bu$_3$SnH for tributyltin hydride; BOP for (benzotriazol-1-yloxy)tris (dimethylamino)phosphonium Hexafluorophosphate; Br$_3$CCO$_2$Na for sodium tribromoacetate; Brine for sodium chloride solution in water; n-BuLi for n-butyl lithium; i-BuLi for i-butyl lithium; t-BuLi for t-butyl lithium; t-BuOH for tert-butanol; Bu$_4$NBr for tetrabutylammonium bromide; Bu$_4$NCl for tetrabutylammonium chloride; Bu$_4$NI for tetrabutylammonium iodide; Cbz for carbobenzyloxy; CDI for carbonyldiimidazole; CH$_2$Cl$_2$ for dichloromethane; ClCH$_2$I for chloroiodomethane; CH$_2$I$_2$ for diiodomethane; CH$_3$ for methyl; CH$_3$CN for acetonitrile; Cl$_3$CCO$_2$Na for sodium trichloroacetate; Cs$_2$CO$_3$ for cesium carbonate; CuCl for copper (I) chloride; CuI for copper (I) iodide; DBU for 1,8-diazabicyclo[5.4.0]undec-7-ene; DCC for N,N'-dicyclohexylcarbodiimide; DCE for 1,2-dichloroethane; DIBAL-H for diisobutylaluminium hydride; DIPEA or (i-Pr)$_2$EtN for N,N-diisopropylethyl amine; Dess-Martin periodinane for 1,1,1-tris(acetyloxy)-1,1-dihydro-1,2-benziodoxol-3-(1H)-one; DMAP for 4-dimethylamino-pyridine; DME for 1,2-dimethoxyethane; DMF for N,N-dimethylformamide; DMSO for dimethyl sulfoxide; EDC for N-(3-dimethylaminopropyl)-N'-ethylcarbodiimide; EDC.HCl for N-(3-dimethylamino-propyl)-N'-ethylcarbodiimide hydrochloride; Et$_2$Zn for diethylzinc; Et$_3$BnNBr for benzyltriethylammonium bromide; EtOAc for ethyl acetate; EtOH for ethanol; Et$_2$O for diethyl ether; Et$_2$Zn for diethyl zinc; Fmoc for 9-fluorenylmethoxycarbonyl; HATU for O-(7-azabenzotriazol-1-yl)-N,N,N',N'-tetramethyluronium hexafluorophosphate; HCl for hydrogen chloride; H$_3$PO$_2$ for hypophosphorous acid; K for potassium; K$_2$CO$_3$ for potassium carbonate; KHMDS for potassium bis(trimethylsilyl)amide; Lombardo reagent for dibromomethane-zinc-titanium(IV) chloride; PhLi for phenyl lithium; LDA for lithium diisopropylamide; Li for lithium; LiHMDS for lithium bis(trimethylsilyl)amide; LiOH for lithium hydroxide; MeOH for methanol; MeI for methyl iodide; Mg for magnesium; Na for sodium; NaBH$_4$ for sodium borohydride; NaBH$_3$CN for sodium cyanoborohydride; NaHMDS for sodium bis(trimethylsilyl)amide; NaCl for sodium chloride; NaClO for sodium hypochlorite; NaH for sodium hydride; NaHCO$_3$ for sodium bicarbonate or sodium hydrogen carbonate; Na$_2$CO$_3$ sodium carbonate; NaOH for sodium hydroxide; NaOMe for sodium methoxide; Na$_2$SO$_4$ for sodium sulfate; NaHSO$_3$ for sodium bisulfite or sodium hydrogen sulfite; Na$_2$S$_2$O$_3$ for sodium thiosulfate; NH$_4$HCO$_3$ for ammonium bicarbonate; NH$_4$Cl for ammonium chloride; NMO for N-methylmorpholine N-oxide; NaIO$_4$ for sodium periodate; o/n for overnight; OH for hydroxyl; OsO$_4$ for osmium tetroxide; Pd for palladium; PDC for pyridinium dichromate; i-PrOAc for isopropyl acetate; Ph for phenyl; PMB for p-methoxybenzyl; rt for room temperature; Ru for ruthenium; SEM for (trimethylsilyl)ethoxymethyl; TBAF for tetrabutylammonium fluoride; TBS for tert-butyl dimethylsilyl; TEA or Et$_3$N for triethylamine; Tebbe reagent for bis(cyclopentadienyl)-μ-chloro(dimethylaluminum)-μ-methylenetitanium; TEMPO for 2,2,6,6-tetramethyl-1-piperidinyloxy, free radical; Teoc for 2-trimethylsilylethoxycarbonyl; TFA or CF$_3$COOH for trifluoroacetic acid; THF for tetrahydrofuran; Ti for titaniumn; TMEDA for N,N, N',N'-tetramethylethylenediamine; TPP or PPh$_3$ for triphenylphosphine; Ts for tosyl or —SO$_2$—C$_6$H$_4$CH$_3$; TsOH for p-tolylsulfonic acid; TMS for trimethylsilyl; TMSCl for trimethylsilyl chloride; TTMSS or (Me$_3$Si)$_3$SiH for tris(trimethylsilyl)silane; V-50 for 2,2'-azobis(2-methylpropion-amidine)dihydrochloride; VA-44 for 2,2'-azobis[2-(2-imidazolin-2-yl)propane]dihydro-chloride; Zhan-1b catalyst for 1,3-bis(2,4,6-trimethylphenyl)-4,5-dihydroimidazol-2-ylidene[2-(iso-propoxy)-5-(N,N-dimethylaminosulfonyl) phenyl]methylene ruthenium(II) dichloride; or Zn for zinc.

All other abbreviations used herein, which are not specifically delineated above, shall be accorded the meaning which one of ordinary skill in the art would attach.

Synthetic Schemes

The present invention will be better understood in connection with Schemes 1-6, wherein R', R, $PG_1$, $PG_2$, PG, $R_1$, $X_1$, $X_2$, and $X_3$ are as previously defined unless otherwise indicated. It will be readily apparent to one of ordinary skill in the art that the process of the present invention can be practiced by substitution of the appropriate reactants and that the order of the steps themselves can be varied.

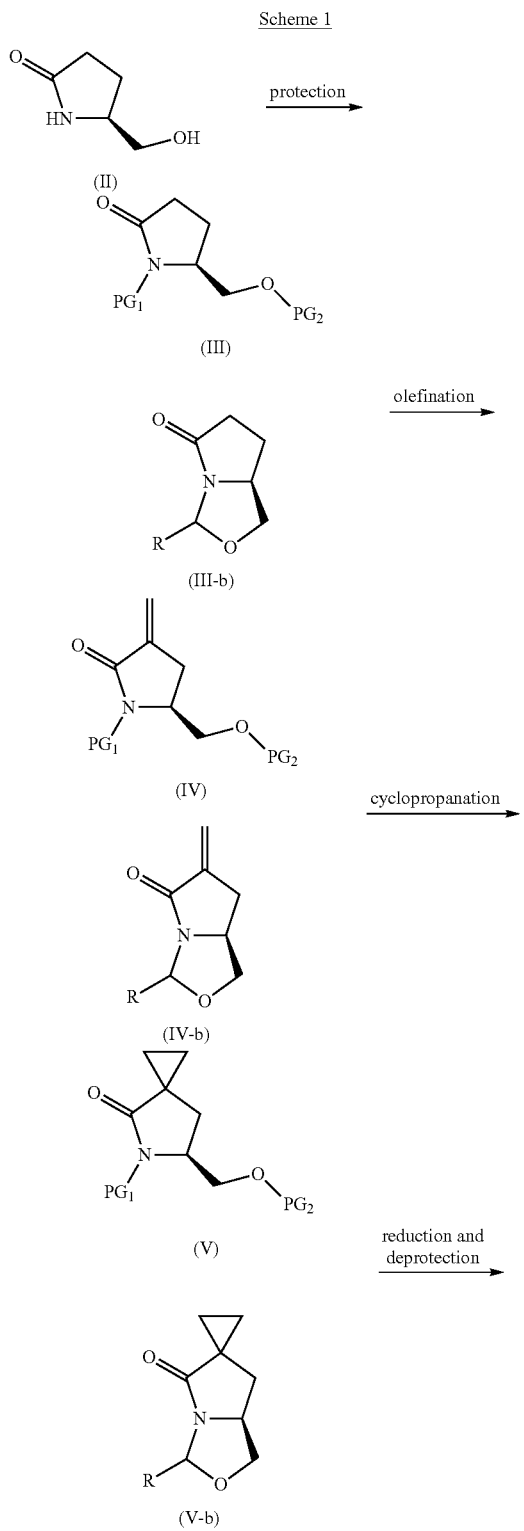

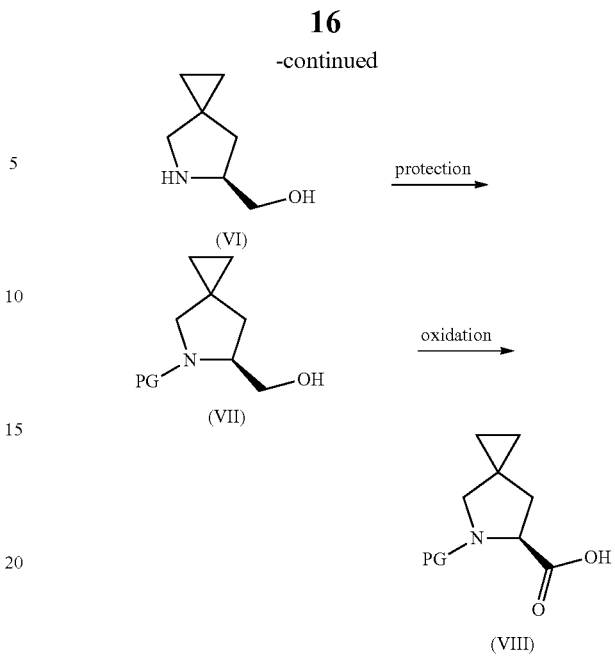

A chemical route to the synthesis of the 4-spirocyclopropyl proline and its derivatives (VIII) is summarized in Scheme 1. (S)-5-(hydroxymethyl)pyrrolidin-2-one (II), which is either commercially available or may be synthesized by methods known to those skilled in the art, may be converted to compounds of formula (III) under conditions known to those skilled in the art. Preferable compounds of formula (III-b) can be prepared by treatment of compound (II) with an aldehyde RCHO, wherein R is as previously defined, in an aprotic solvent such as, but not limited to, toluene, xylenes, and mesitylene. The reaction is typically conducted at a temperature of about 85° C. to about 110° C. with azeotropically water removal apparatus such as Dean-Stark trap. The reaction time is typically 10 to 20 hours.

Compounds of formulae (III) or (III-b) may be transformed to compounds of formulae (IV) or (IV-b) in three steps: 1) treatment of compounds of formulae (III) or (III-b) with a base, such as, but not limited to, LiHMDS, NaHMDS, KHMDS, nBuLi, LDA, or NaH, to form a lactam enolate. This process is carried out in an aprotic solvent such as, but not limited to, THF, 2-methyltetrahydrofuran, or DMF. The typical reaction temperature is about −100° C. to about 0° C. and reaction time is typically 1 to 3 hours; 2) treatment of the lactam enolate with Eschenmoser's salt, or the like, to provide alkylated or dialkylated lactam. The typical reaction temperature is about −100° C. to about 40° C. and reaction time is typically 1 to 12 hours. Step 1) and step 2) are typically carried out in a one-pot process; 3) treatment of the alkylated or dialkylated lactam with methyl iodide or other quaternization reagent to provide compounds of formulae (IV) or (IV-b) in the presence of a base such as $NaHCO_3$, $KHCO_3$, or the like, in an alcoholic solvent. The typical reaction temperature is about 20° C. to about 50° C. and reaction time is typically 1 to 12 hours.

Compounds of formulae (IV) or (IV-b) may be converted to compounds of formulae (V) or (V-b) by reaction with a sulfuonium or sulfoxonium glide, which may be generated in situ by treatment of either trialkylsulfonium or trialkylsulfoxonium halide with a base (Corey-Chaykovsky Reaction). Other substituted sulfur ylides, such as, but not limited to, aminosulfoxonium ylides, may be used. Preferably dimethylsulfoxonium methylide is used and prepared from trimethylsulfoxonium iodide and a base, such as, but not limited to NaH, n-BuLi, NaOMe, $NaNH_2$, or KOtBu. The reaction typically takes place in an aprotic solvent, such as, but not limited to DMSO, DMF, THF, dichloromethane, and toluene. The reaction temperature is typically about 10° C. to about 70° C. and the reaction time is typically 3 to 12 hours.

A compound of formula (V) may be converted to a compound of formula (VI) in two steps: 1) reduction of the lactam in formula (V) to produce a proline derivative; 2) removal of the N- or O-protecting groups. Alternatively, the order of reduction and deprotection can be switched using similar procedures known to those skilled in the art. Preferably a compound of formula (V-b) is converted to a compound of formula (VI) by 1) reduction with a reducing agent such as, but not limited to, $LiAlH_4$, $AlH_3$, or a borane to provide an N-alkyl protected proline derivative. The reaction typically takes place in an aprotic solvent, such as, but not limited to an ether, THF, or toluene. The reaction temperature is typically about 10° C. to about 70° C. and the reaction time is typically 3 to 12 hours; 2) deprotection of the N-protected proline to produce a compound of formula (VI). Reaction conditions vary depending on the choice of the deprotecting group and will be known to those skilled in the art. Preferably, if R is aryl or substituted aryl, the deprotection is achieved by catalytic hydrogenolysis or transfer hydrogenolysis in the presence of a metallic catalyst such as, but not limited to, palladium (0), platinum (0), ruthenium (0), $Pd(OH)_2$, or $Pt(OH)_2$, and a hydrogen source such as, but not limited to, hydrogen, diimide, cyclohexene, ammonium formate, or ammonium bicarbonate. The reaction typically takes place in an alcoholic solvent. The reaction temperature is typically about 10° C. to about 70° C. and the reaction time is typically 3 to 12 hours. Alternatively, the compound of formula (VI) is prepared by 1) deprotection of a compound of formula (V-b) in the presence of an acid such as, but not limited to, trifluoroacetic acid, toluenesulfonic acid, methanesulfonic acid, camphorsulfonic acid, or HCl, to provide lactam

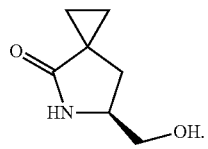

The reaction typically takes place in an alcoholic solvent. The reaction temperature is typically about 10° C. to about 80° C. and the reaction time is typically 3 to 24 hours; and 2) reduction of the lactam to the compound of formula (VI) using procedures similar to those described above.

A compound of formula (VI) can be converted to a compound of formula (VII) by protection of the amino group. Reaction conditions vary depending on the choice of the protecting group and will be known to those skilled in the art, and are described generally in T. H. Greene and P. G. M. Wuts, *Protective Groups in Organic Synthesis,* 3rd edition, John Wiley & Sons, New York (1999). Preferably, PG is Boc or Cbz.

A compound of formula (VII) can be converted to a compound of formula (VIII) by treatment with an oxidizing reagent, such as but not limited to chromium(VI) reagents, permanganates, or $NaClO_2$. A comprehensive list of oxidizing reagents and conditions may be found in *Comprehensive Organic Transformations* (R. C. Larock, 2nd ed. page 1653-1655). The reaction typically takes place in a protic solvent. The exact reaction conditions and times will vary with the choice of the oxidizing reagents and will be known to those skilled in the art. The oxidizing reagent is preferably the Jones reagent, the solvent is preferably water in acetone and the reaction time is typically 1 to 5 hours. Alternatively, a compound of Formula (VII) can be converted to a compound of Formula (VIII) in two steps: 1) oxidation of the compound of formula (VII) to the corresponding aldehydes with an oxidizing reagent, such as, but not limited to PDC, Dess-Martin periodinane, and that used in Swern oxidation or Corey-Kim oxidation in an aprotic solvent. A comprehensive list of oxidizing reagents and conditions may be found in *Comprehensive Organic Transformations* (R. C. Larock, 2nd ed. page 1234-1249); and 2) oxidation of the aldehyde of step 1) to produce a compound of formula (VIII) by treatment with an oxidizing reagent, such as but not limited to chromium(VI) reagents, permanganates, or $NaClO_2$ similar to those previously described.

Scheme 2

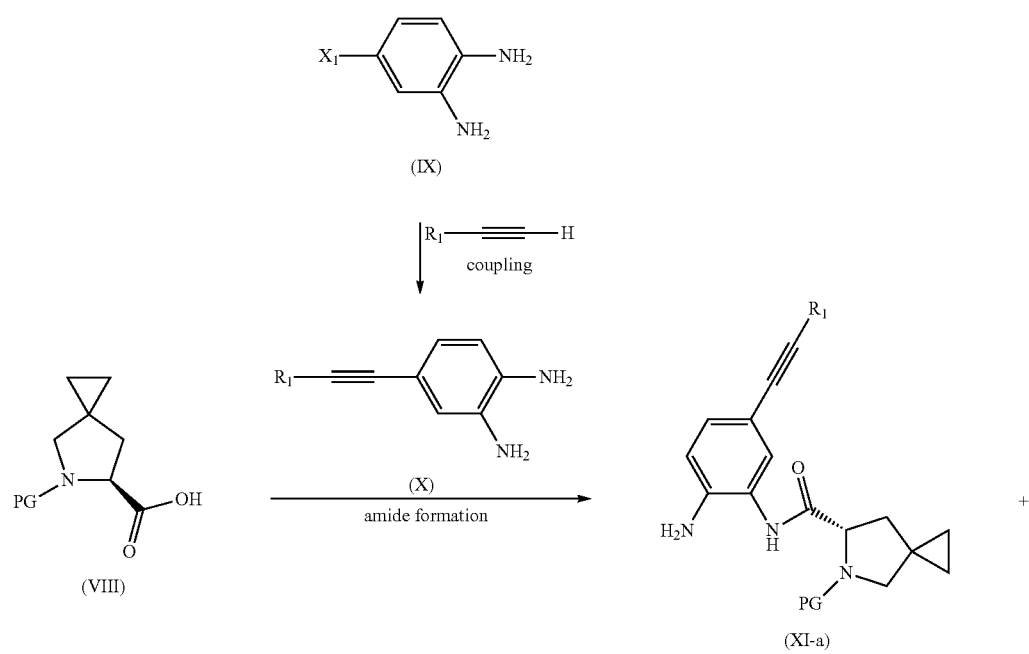

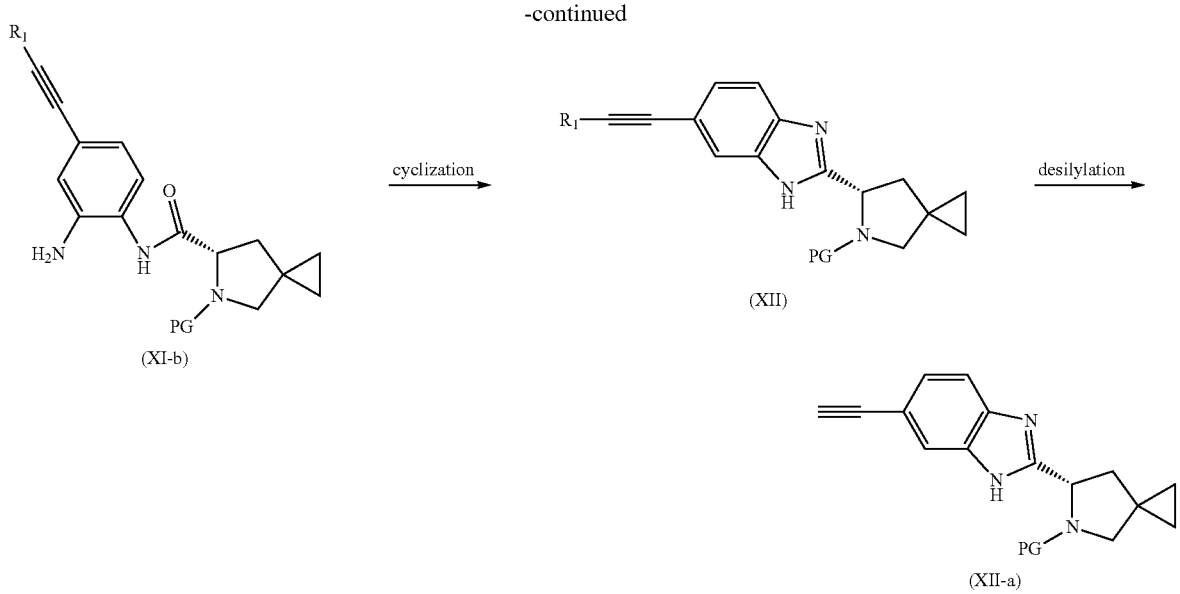

Scheme 2 illustrates the synthesis of compounds of formula (XII-a). A compound of formula (IX), which is either commercially available or can be synthesized by methods known to those skilled in the art, can be converted to a compound of formula (X) by reacting with R₁—≡—H in the presence of a palladium catalyst, a copper catalyst, and a base (Sonogashira cross-coupling). Suitable palladium catalysts for this process include, but are not limited to, tetrakis(triphenylphospine)palladium (0), tris(dibenzylideneactone)dipalladium (0) (Pd$_2$(dba)$_3$), palladium (II) acetate, and tetradi(benzylideneactone)dipalladium. Suitable copper catalysts for this process include, but are not limited to, copper (I) iodide, copper (I) bromide, and copper (I) cyanide. Suitable bases include, but are not limited to, triethylamine, diisopropylethylamine, and diisopropylamine. This process is carried out in an aprotic solvent, such as, but not limited to, acetonitrile, THF, DMF, ethyl acetate, or isopropyl acetate. The reaction temperature is typically about 10° C. to about 50° C. and the reaction time is typically 1 to 3 hours.

A compound of formula (X) can be converted to a mixture of compounds of Formulae (XI-a) and (XI-b) by coupling with a compound of formula (VIII) in the presence of an amide coupling agent such as 1,1'-carbonyldiimidazole, bis(2-oxo-3-oxazolidinyl)phosphinic chloride, 1-hydroxy-7-azabenzotriazole, 1-hydroxybenzotriazole hydrate, 3-hydroxy-1,2,3-benzotriazin-4(3H)-one, 1-(3-dimethyaminopropyl)-3-ethylcarbodiinide hydrochloride, 4-nitrophenol, pentafluorophenol, 2-hydroxypyridine, N-hydroxysuccinimide, N-hydroxyphthalamide, 2-mercaptobenzoxazole, trimethylacetyl chloride, isobutylchloroformate, chlorodimethoxytriazole, oxalyl chloride, 2-hydroxypyridine-N-oxide, 5-nitro-2-hydroxypyridine, Boc-L-valine anhydride, and mixtures thereof. Examples of suitable solvents include, but are not limited to, isopropyl acetate, ethyl acetate, dichloromethane, acetone, THF, NMP, 2-methyltetrahydrofuran, and acetonitrile. Particular conditions will vary depending on the nature of the coupling reagent and will be known to those of ordinary still in the art.

The mixture of compounds of formulae (XI-a) and (XI-b) can be converted to compounds of formula (XII) in the presence of an acid, such as, but not limited to, acetic acid. An aprotic solvent, such as, but not limited to, toluene or xylenes, can be used. The reaction temperature is typically about 40° C. to about 70° C. and the reaction time is typically 3 to 8 hours.

If R₁ is a silyl group, the compound of formula (XII) can be converted to a compound of formula (XII-a) by treatment with a base such as, but not limited to, K$_2$CO$_3$, Na$_2$CO$_3$, or Cs$_2$CO$_3$ in an alcoholic solvent such as, but not limited to, methanol, ethanol, isopropanol or butanol. The reaction temperature is typically about 20° C. to about 40° C. and the reaction time is typically 1 to 4 hours.

Scheme 3

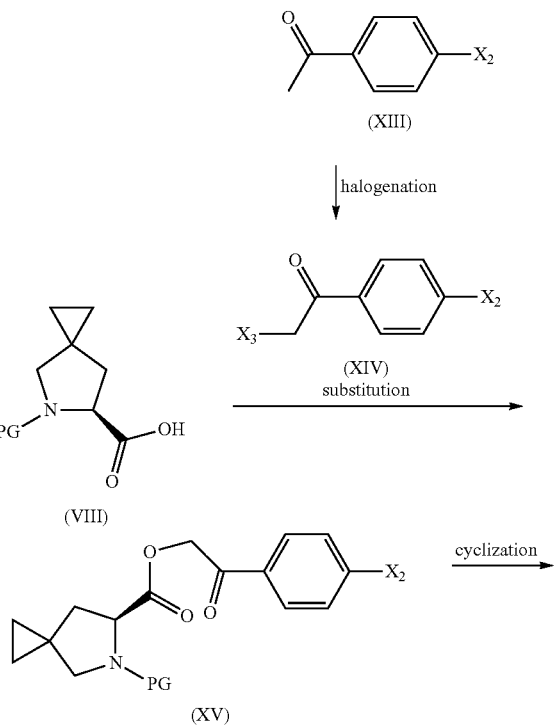

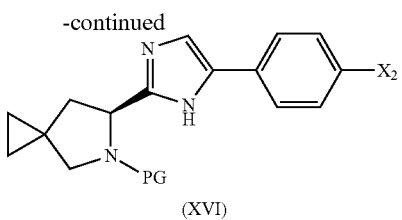

(XVI)

Scheme 3 illustrates the synthesis of compounds of formula (XVI). A compound of formula (XIII), which is either commercially available or can be synthesized by methods out in an aprotic solvent, such as, but not limited to, acetonitrile, THF, DMF, DMSO, NMP, acetone, dichloromethane, ethyl acetate or isopropyl acetate. The reaction temperature is typically about 20° C. to about 40° C. and the reaction time is typically 1 to 12 hours.

The compound of formula (XV) can be converted to a compound of formula (XVI) by treatment with ammonium acetate, ammonium formate, ammonium sulfamate, ammonium phosphate, ammonium citrate, ammonium carbamate, or ammonia in a solvent such as, but not limited to, toluene, xylenes, mesitylene or acetic acid. The reaction is typically conducted at a temperature of about 85° C. to about 110° C. and reaction time is typically 10 to 20 hours.

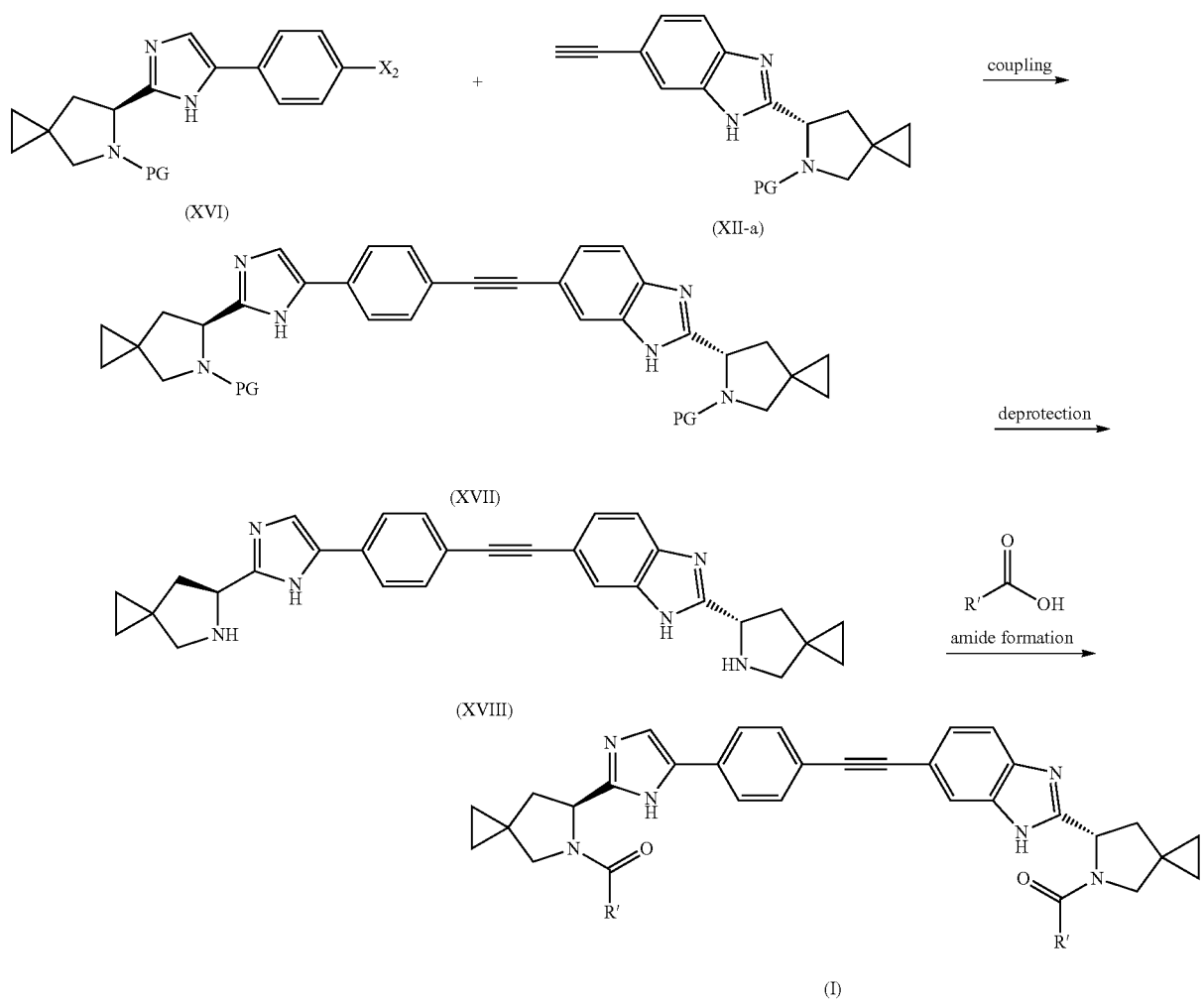

Scheme 4 known to those skilled in the art, can be converted to a compound of formula (XIV) by reacting with a halogenating reagent such as, but not limited to, bromine, iodine, NBS, NBS or NIS in a solvent such as, but not limited to, dichloromethane, toluene, or acetic acid. The reaction temperature is typically about 20° C. to about 40° C. and the reaction time is typically 1 to 4 hours.

The compound of formula (XIV) can then react with a compound of formula (VIII) in the presence of a non-nucleophilic base to provide a compound of formula (XV). Suitable bases include, but are not limited to, triethylamine, diisopropylethylamine, and diisopropylamine. This process is carried Scheme 3 illustrates the synthesis of compounds of formula (I). Compounds of formula (XVI) can react with compounds of formula (XII-a) in the presence of a palladium catalyst, a copper catalyst, and a base (Sonogashira cross-coupling). The metallic catalysts, bases, solvents and reaction conditions can be selected similarly as those described in the preparation of compounds of formula (X) in Scheme 2.

A compound of formula (XVIII) can be prepared by deprotection of the protecting group contained in the compound of formula (XVI). Reaction conditions vary depending on the choice of the deprotecting group and will be known to those skilled in the art, and are described generally in T. H. Greene and P. G. M. Wuts, *Protective Groups in Organic Synthesis*, 3rd edition, John Wiley & Sons, New York (1999). Representative deprotecting agents include HCl for Boc protecting group.

The compound of formula (XVIII) can be converted to compounds of formula (I) by coupling with an appropriately substituted amino acid in the presence of coupling agents. The coupling reagents and reaction conditions can be selected similarly to those described in the preparation of a mixture of compounds of formulae (XI-a) and (XI-b) in Scheme 2.

Scheme 5

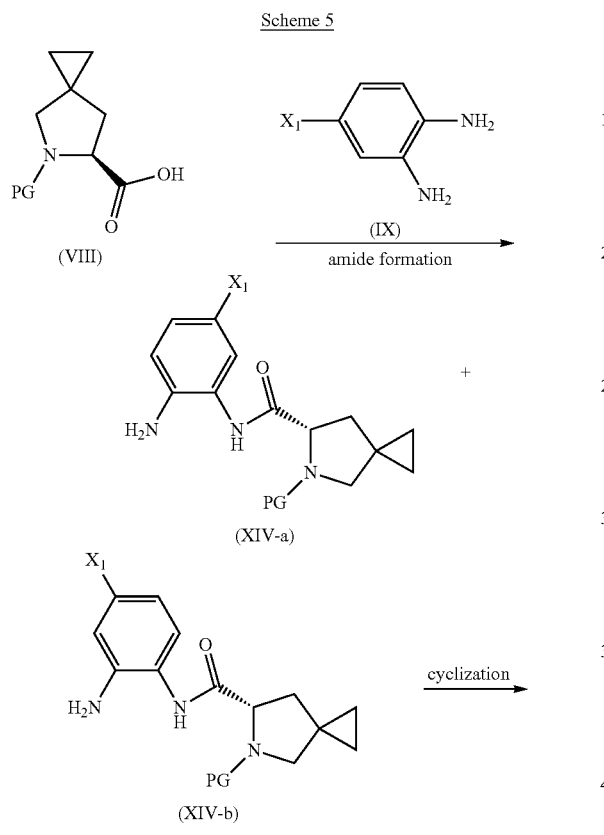

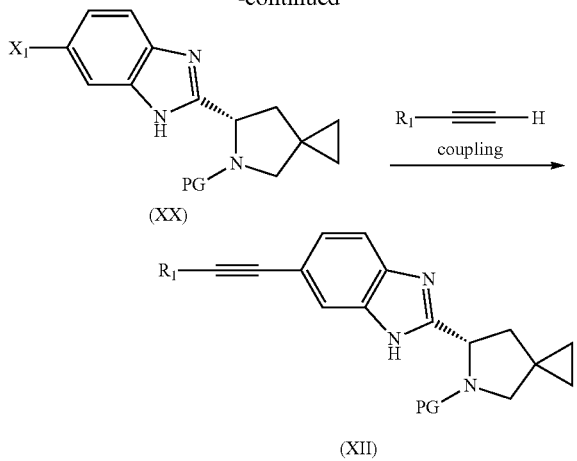

Scheme 5 illustrates an alternative synthesis of the compound of formula (XII). The compound of formula (VIII) can react with the compound of formula (IX) in the presence of an amide coupling agent to provide a mixture of compounds of formulae (XIV-a) and (XIV-b). The coupling agents and reaction conditions can be selected similarly as those described in the preparation of a mixture of compounds of formulae (XI-a) and (XI-b) in Scheme 2.

The mixture of compounds of formulae (XIV-a) and (XIV-b) can be converted to a compound of formula (XX) in the presence of an acid, such as but not limited to, acetic acid. An aprotic solvent, such as, but not limited to, toluene, or xylenes, may be used. The reaction temperature is typically about 40° C. to about 70° C. and the reaction time is typically 3 to 8 hours.

The compound of formula (XX) may be converted to the compound of formula (XII) by reacting with $R_1$—≡—H the presence of a palladium catalyst, a copper catalyst, and a base (Sonogashira cross-coupling). The metallic catalysts, bases, solvents and reaction conditions can be selected similarly as those described in the preparation of compounds of formula (X) in Scheme 2.

Scheme 6

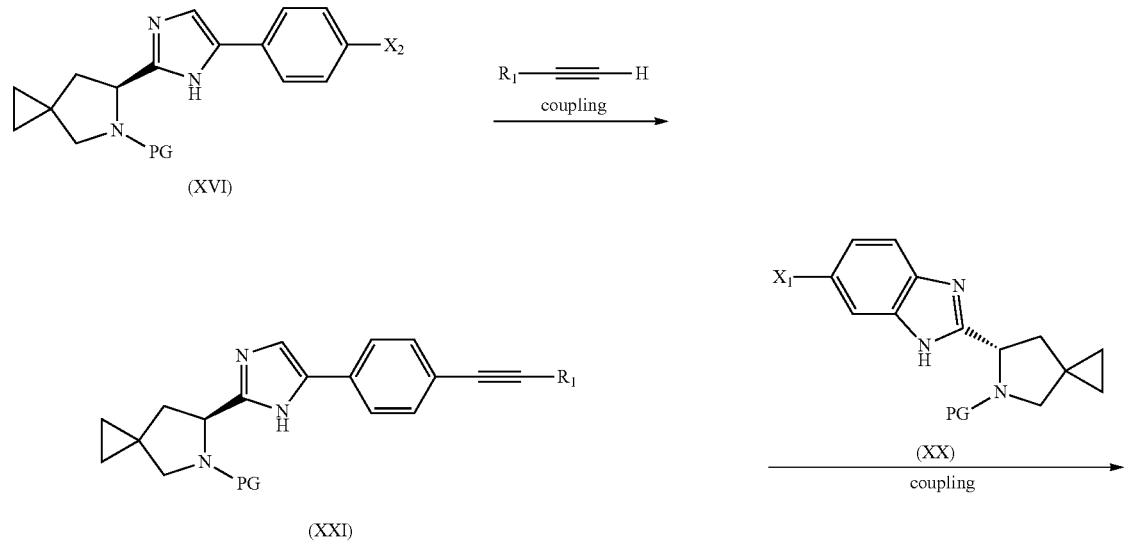

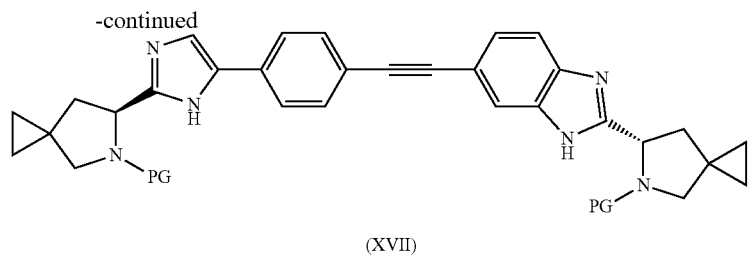

(XVII)

Scheme 6 illustrates an alternative synthesis of the compound of formula (XVII). The compound of formula (XVI) may be converted to a compound of formula (XXI) by reacting with R₁—≡—H in the presence of a palladium catalyst, a copper catalyst, and a base (Sonogashira cross-coupling). The metallic catalysts, bases, solvents and reaction conditions can be selected similarly as those described in the preparation of compounds of formula (X) in Scheme 2.

The compound of formula (XXI) may be converted to the compound of formula (XVII) by reacting with R₁—≡—H in the presence of a palladium catalyst, a copper catalyst, and a base (Sonogashira cross-coupling). The metallic catalysts, bases, solvents and reaction conditions can be selected similarly as those described in the preparation of compounds of formula (X) in Scheme 2.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

Preparation of (S)-2-Methoxycarbonylamino-1-((S)-6-(5-(4-((2-((S)-5-((S)-2-methoxycarbonylamino-3-methylbutanoyl)-5-azaspiro[2.4]heptan-6-yl)-1H-benzo[d]imidazol-6-yl)ethynyl)phenyl)-1H-imidazol-2-yl)-5-azaspiro[2.4]heptan-5-yl)-3-methylbutan-1-one Step 1: Synthesis of (3R,7aS)-3-phenyltetrahydropyrrolo[1,2-c]oxazol-5(1H)-one

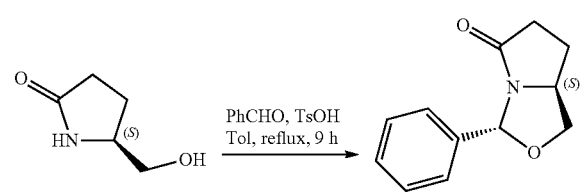

Toluene (36 L, 6 vol), L-pyroglutaminol (6.0 Kg, 1.0 eq), benzaldehyde (8.3 Kg, 1.5 eq) and p-toluenesulfonic acid (134 g, 1.5% mol) were charged to a reactor. The resulting mixture was heated to reflux and the water formed during the reaction was separated out by using Dean-Stark condenser. The completion of the reaction was monitored by HPLC until L-pyroglutaminol was ≤0.1%. It was cooled to 15~20° C., added aqueous 5% NaHCO₃ (3 vol), agitated for 15 min and separated the layers. 20% aqueous NaHSO₃ (6 vol) was charged to the organic phase, upon stirring for 30 min, filtered through Celite and washed the cake with toluene. Separated the organic phase (this step could be skipped if there was no solid), and filtered the organic phase through a thin pad of silica gel (1.0 wt/wt) and washed the silica gel with toluene three times. Combined the organic phase and monitored by HPLC. If impurity (RRT=1.5)>1.5%, repeated the silica gel filtration procedures until the impurity (RRT=1.5)≤1.5%. Dried the filtrate with anhydrous Na₂SO₄ for at least 2 hrs, filtered and washed the cake with toluene for twice. Concentrated below 55° C. (bath temp) under vacuum to afford 8.30 kg (78.6% yield) of the title compound with 94.6% HPLC purity. ESI MS m/z (M+H)⁺ 204.11.

Step 2: Synthesis of (3R,7aS)-6-methylene-3-phenyltetrahydropyrrolo[1,2-c]oxazol-5(1H)-one

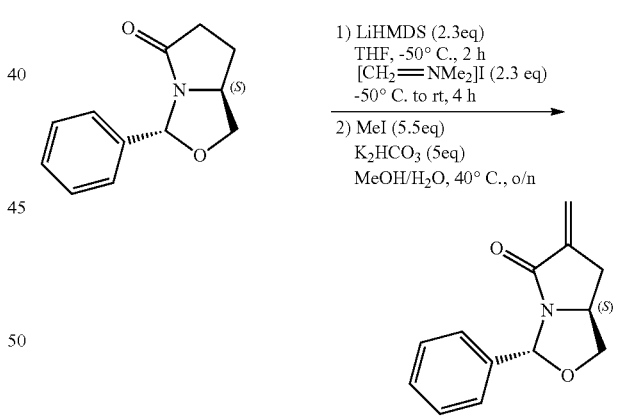

(3R,7aS)-3-phenyltetrahydropyrrolo[1,2-c]oxazol-5(1H)-one (4.5 Kg, 1.0 eq) was dissolved in anhydrous THF (13.5 L, 3 vol) and added to a dropping funnel. Separately, LiHMDS/THF solution (2.3 eq) was charged to a reactor and cooled to −50 to −40° C. Then dropwise added the above (3R,7aS)-3-phenyltetrahydropyrrolo[1,2-c]oxazol-5(1H)-one/THF solution while maintaining the reaction temperature at −50 to −40° C. Kept stirring at −50 to −40° C. for additional 2 hrs and then further cooled to −55 to −45° C. Eschenmoser's salt (2.3 eq) was added in portions while maintaining the reaction temperature at −55 to −45° C. and then keep stirring for additional 30 mins upon the completion of Eschenmoser's salt addition. The reaction mixture was slowly warmed to 10~15° C. within 3~4 hrs. The completion of reaction was evidenced by HPLC (starting material ≤2.0% after 3 hrs of the addition of Eschenmoser's salt). Charged water (9 L, 2 vol) and agitated for 15 mins. The mixture was concentrated under vacuum below 40° C. (bath temp) until distillate ceased. Cooled to 25~30° C. and collected the bis-alkylated intermediate (>80% HPLC purity) into a plastic drum. The reactor was rinsed with methanol (6.8 L×2) and combined with the above intermediate. ESI MS m/z (M+H)+ 318.28.

Methanol (3 vol), the above intermediate, iodomethane (5.5 eq), potassium bicarbonate (4.0 eq) and water (2 vol) were charged to a reactor while maintaining the temperature at 10~15° C. The resulting mixture was slowly warmed to 35~50° C. within a period of 1 to 1.5 h and kept stirring at 35~50° C. for 18 h. The completion of reaction was monitored by HPLC every 2 hrs until the conversion was 99+%. Concentrated below 50° C. (bath temp) until there distillate almost ceased. The residue was mixed with EtOAc, stirred for 20 mins, filtered and washed with EtOAc (2 vol×2). The combined filtrate was separated and the aqueous phase was exacted with EtOAc (3 vol×2). The combined organic phase was washed with brine (6 vol), dried over anhydrous sodium sulfate (2 wt/wt), filtered and washed the cake with EtOAc (2 vol×2). The combined filtrate was concentrated at 35~45° C. under vacuum until distillate almost ceased. The residue was cooled to 15~25° C., added MTBE (6 vol), stirred for 30 min, filtered and washed the solid cake with MTBE (2 vol×2). The combined filtrate was concentrated below 45° C. until distillate almost ceased. Collected the product into the plastic drum. The yield was 51.5% for this 2-step reaction process. ESI MS m/z (M+H)+ 216.12.

Step 3: Synthesis of (3'R,7a'S)-3'-phenyldihydro-1'H-spiro[cyclopropane-1,6'-pyrrolo[1,2-c]oxazol]-5'(3'H)-one

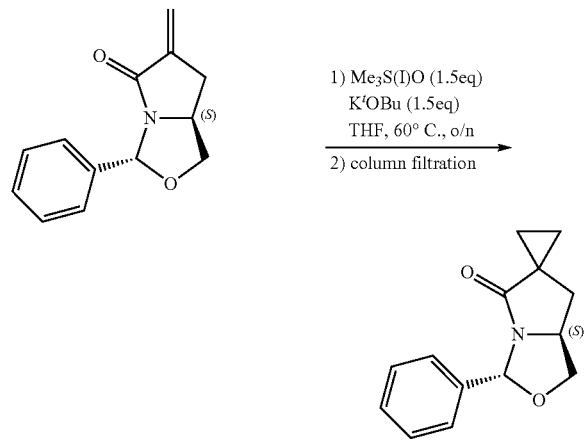

Trimethylsulfoxonium iodide [Me₃S(O)I] (1.5 eq) and anhydrous THF (12 vol) were charged to a reactor. Cooled to 10~20° C. and then added t-BuOK (1.5 eq). The resulting mixture was warmed to 60±5° C. and stirred for 1 h. Cooled down back to 10~20° C. and then dropwise added a solution of (3R,7aS)-6-methylene-3-phenyltetrahydropyrrolo[1,2-c]oxazol-5(1H)-one (1.0 eq) in THF (3 vol) while maintaining the temperature at 60±5° C. The completion of reaction was monitored by HPLC every hour until the conversion >99% (system purity was 55%~60%). The reaction mixture was then cooled to 15~20° C., filtered and washed the cake with EtOAc (2 vol). The combined filtrate was washed with brine (3 vol) and the aqueous phase was back-extracted with EtOAc (3 vols). The combined organic phase was concentrated to about 3 vol under vacuum below 45° C. Add silica gel (1 wt/wt) and continued to concentrate to almost dryness. The solid residue was purified by silica gel (2 wt/wt) chromatography eluting with petroleum ether (PE) followed by EtOAc/PE=1:10 (v/v). The yield was about 40% (97.1% HPLC purity). ESI MS m/z (M+H)+ 230.16.

Step 4: Synthesis of (S)-5-azaspiro[2.4]heptan-6-ylmethanol

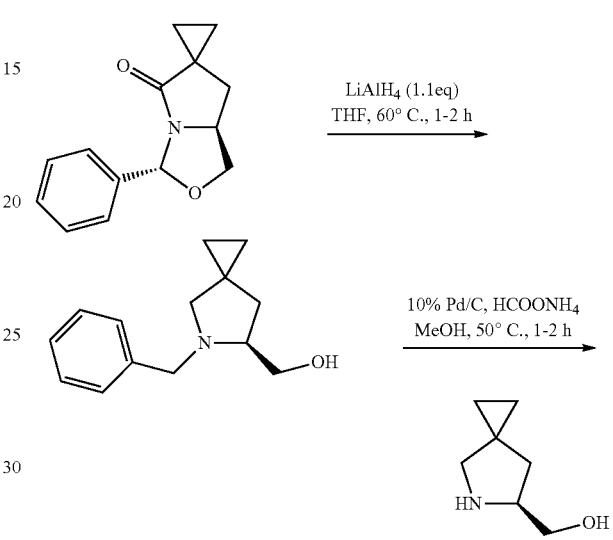

This is a 2-step reaction sequence process. First, to a solution of (3'R,7a'S)-3'-phenyldihydro-1'H-spiro[cyclopropane-1,6'-pyrrolo[1,2-c]oxazol]-5'(3'H)-one (1.83 kg, 7.984 mol, 1 equiv.) in anhydrous THF (7 L) was added 1M LAH solution in THF (8.72 L, 8.72 mol, 1.09 equiv.) during a period of about 30 min. The internal temperature was increased up to about 50° C. over the period of LAH addition. After agitating the mixture at the reflux temperature (about 60° C.) for about 60 min, the reaction was completed as evidenced by MS. Upon cooling, it is quenched with water (330 ml) over a period of 15 to 20 min at below 25° C. [CAUTION: lots of gas evolution!] and followed by 15% (wt/vol) aqueous NaOH (330 ml), and finally with water (990 ml) and controlled the temperature at about 20 to 25° C. during the quench. The quenched white suspension was filtered and the cake was washed with THF (12 L). The combined THF solution was rotavapped and chased with MeOH (2 L) to afford 1.78 kg yellowish oil ((S)-(5-benzyl-5-azaspiro[2.4]heptan-6-yl)methanol). Without purification, it was directly used for the next reaction. ESI MS m/z (M+H)+ 218.14.

10% Pd/C (85 g, 4.6 wt % to the tricyclic starting material EP-019647) in a 1 L beaker was wetted with water (500 ml, 5.9 vols to Pd/C) and transferred to a N₂ purged reactor. Under N₂, charged MeOH (4 L) followed by ammonium formate (1.5 kg, 23.787 mol, 2.98 equiv.). The internal temperature was below 10° C. at the point. The mixture was charged more MeOH (4 L) and then heated to about 15° C. and charged a solution of above (S)-(5-benzyl-5-azaspiro[2.4]heptan-6-yl) methanol (1.78 kg) in MeOH (4 L). The resulting mixture was slowly heated to about 50° C. over the period of about 60 to 80 min. It was kept at this temperature for an additional 60 min at which point the reaction was complete as evidenced by NMR/MS/TLC. Upon cooling down, it was filtered through a pad of celite and the cake washed with DCM (8 L). The filtrate was rotavapped and chased with DCM (8 L) to afford the title compound as a yellowish thick oil. Without purification, it was used directly for the next step. ESI MS m/z (M+H)+ 128.13.

Step 5: Synthesis of (S)-tert-butyl 6-(hydroxymethyl)-5-azaspiro[2.4]heptane-5-carboxylate

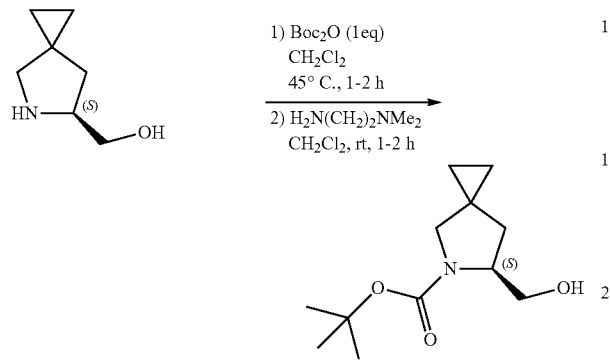

A solution of (S)-5-azaspiro[2.4]heptan-6-ylmethanol in DCM (4 L) is charged with a solution of di-tert-butyl dicarbonate (1.4 kg, 6.415 mol, 0.8 equiv. to EP-019647) in DCM (2 L). The resulting mixture was heated at the bath temperature 45° C. for 60 min. It was rotavapped and NMR showed the reaction was not complete. After recharging DCM (4 L) and agitated at the ambient temperature overnight, it was rotavapped and charged more di-tert-butyl dicarbonate (100 g, 0.458 mol, 0.06 equiv. to EP-019647) in DCM (4 L) and heated at 40 to 45° C. for 60 min. It was rotavapped and the residual dissolved in EtOAc (15 L), washed with 0.5N HCl (6 L) and with water (4 L), and with aqueous NaHCO₃ (4 L), and finally with brine (4 L). After polish filtration, it was rotavapped and pump-dried to afford 1.434 kg of the title compound as a thick oil. The yield was 79% from (3'R,7a'S)-3'-phenyldihydro-1'H-spiro[cyclopropane-1,6'-pyrrolo[1,2-c]oxazol]-5'(3'H)-one. The corrected yield was about 71% due to ~10% di-tert-butyl dicarbonate contamination.

To remove some excess (typically in the range of 5 to 10%) di-tert-butyl dicarbonate in the product: it was further treated with N.N-dimethylethylenediamine (1.8 to 2 equiv. to the amount of the Boc-anhydride) in DCM (2.2 vols) at the ambient temperature for 30 to 60 min. The mixture was rotavapped and solvent swap to EtOAc (3 vols), washed with 1N HCl (1.2 vols), and followed with 15% aqueous NaCl (1.2 vols×2), and finally with a mixture of aqueous sodium bicarbonate and brine (1:1, 1.2 vols). It was rotavapped to dryness and chased with EtOAc and pump-dried to afford purified title compound as a thick yellowish/orange oil. ESI MS m/z (M-ᵗBu+H)+ 172.10.

Step 6: Synthesis of (S)-5-(tert-butoxycarbonyl)-5-azaspiro[2.4]heptane-6-carboxylic acid

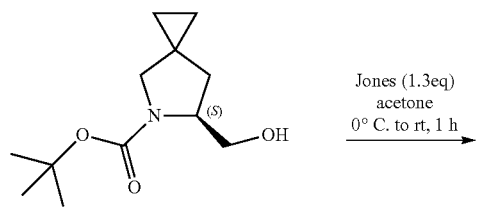

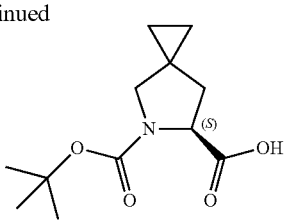

Preparation of Jones reagent (2.54M chromium trioxide in 4.1M sulfuric acid): To a stirring H₂O (3.2 L) was charged portionwise solid CrO₃ (2.14 kg, 21.4 mol, highly toxic!). Under cooling (ice-water bath), it was slowly charged 95~98% H₂SO₄ (1.84 L) via a dropping funnel during which period the temperature increased up to 35° C. Upon cooling to about 15° C., it was further charged more H₂O (2.96 L) to give about 8.4 L of the Jones reagent at the concentation of about 2.54M.

A solution of the (S)-tert-butyl 6-(hydroxymethyl)-5-azaspiro[2.4]heptane-5-carboxylate (1.0 kg, 4.399 mol, 1 equiv.) in acetone (10 L) was cooled to about 0~5° C. and was added dropwise Jones reagent (2.54M chromium trioxide in 4.1M sulfuric acid, 2.25 L, about 1.3 equiv.) during the period of about 60 min. This addition was exothermic and the reaction temperature was gradually increased up to 33 to 37° C. upon the completion of the Jones reagent. The reaction was complete within 60 min as evidenced by NMR/TLC. It is then quenched with IPA (1 L) for 15 min to give a upper clear solution and a lower layer as solid. The upper clear solution was decanted and concentrated in vacuo to leave an oil-like residue which contained the most of the product. The solid was disolved in water (10 vols) and combined with the above concentrated residue oil. The mixture was extracted with toluene twice (6 vols+2 vols). The combined toluene solution was washed with brine (2 vols) to give the crude product solution in toluene. Chemical purification: The toluene solution containing the amino acid product was extracted twice into 1M NaOH (6 vols+3 vols) as its sodium salt, and then released with 6M HCl (about 1.6 L needed to adjust pH to 2) at 20 to 15° C. and extracted twice with EtOAc (6 vols+3 vols), washed with brine (2 vols) and dried over Na₂SO₄. After filtration, it was rotavapped to the dryness to afford the title compound as an oil and soon solidified as an off-white solid. The yield was 0.74 kg (70% yield) after vacuum drying. ¹H NMR (500 MHz, CDCl₃): 4.51-4.42 (m, 1H), 3.48-3.11 (m, 2H), 2.27-1.93 (m, 2H), 1.50/1.45 (two overlapping s, 9H), 0.71-0.59 (m, 4H).

Step 7: Synthesis of 4-((trimethlsilyl)ethynyl)benzene-1,2-diamine

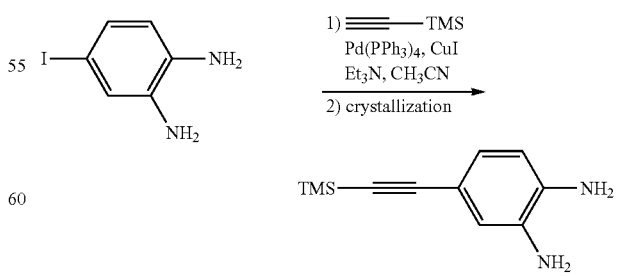

A solution of 4-iodo-1,2-diaminobenzene (1.57 kg, 6.708 mol, 1 equiv.) in anhydrous MeCN (10 L) was charged (trimethylsilyl)acetylenene (1.0 L, 7.178 mol, 1.07 equiv.) and TEA (2.95 L, 21.14 mol, 3.15 equiv.). The resulting mixture was degassed by bubbling N$_2$ for about 20 min and while keeping the N$_2$ bubbling, charged catalyst Pd(PPh$_3$)$_4$ (150 g, 0.130 mol, 1.9 mol %) and followed by CuI (46 g, 0.241 mol, 3.6 mol %). The reaction started immediately and was exothermic up to about 60° C. within 20 min. The reaction was complete in 30 to 60 min as evidenced by MS and TLC. The reaction mixture was rotavapped and solvent swapped to EtOAc (8 L), and washed with aqueous NaHCO$_3$ solution (8 L). Upon drying over Na$_2$SO$_4$, it was filtered through a pad of celite and concentrated to small volume and then charged hexanes (6 L) to crystallize the product. The slurry was agitated at the ambient temperature for at least 2 hrs before filtration and washing (EtOAc/Hex., 1:10) and drying to afford 1.2 kg (88% yield) of grey title compound. ESI MS m/z (M+H)$^+$ 205.11.

Step 8: Synthesis of (S)-tert-butyl 6-((6-((trimethylsilyl)ethynyl)-1H-benzo[d]imidazol-2-yl)-5-azaspiro[2.4]heptane-5-carboxylate

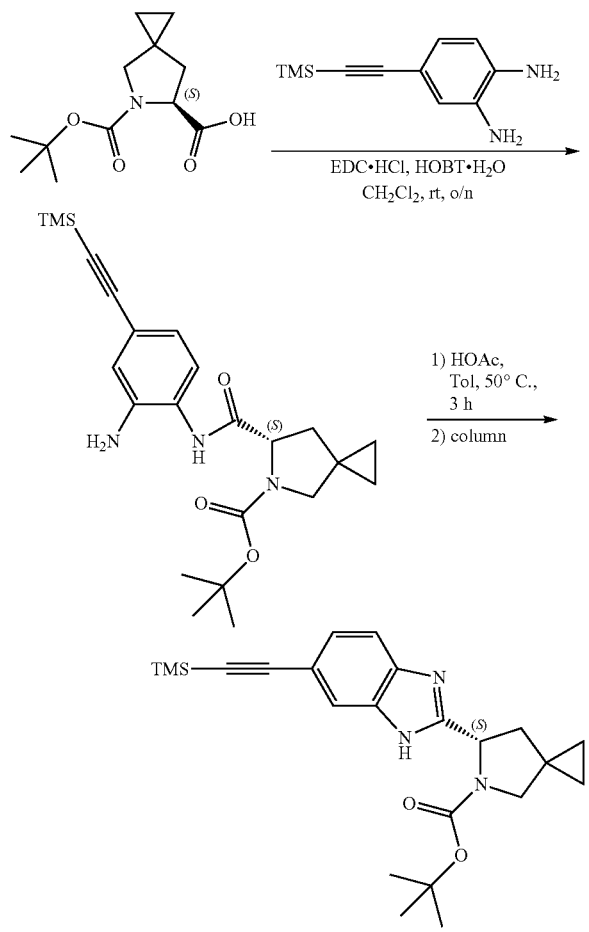

To a clear solution of (5)-5-(tert-butoxycarbonyl)-5-azaspiro[2.4]heptane-6-carboxylic acid (0.97 kg, 4.02 mol, 1 equiv,) in DCM (10 L) was charged HOBT hydrate (0.75 kg, 4.458 mol, 1.1 equiv.) to give a light brown suspension. It was further charged EDC.HCl (0.95 kg, 4.955 mol, 1.23 equiv.) and the resulting brown opaque mixture was agitated at the ambient temperature for 30 to 45 min. Then it was treated with a suspension of 4-TMS(Acetylene)benzenediamine (1.12 kg, 5.48 mol, 1.36 equiv.) in DCM (1 L). The mixture was agitated at the room temperature overnight. It was filtered through a pad of silica gel (350 g) and celite and washed with DCM (8 L). The organic filtrate was washed with aq. NaHCO$_3$ (8 L). The aqueous layer was back-extracted with DCM (8 L) to recover small amount of the product. After drying (Na$_2$SO$_4$), it was rotavapped and chased with toluene (4 L) to afford about 2.4 kg (not fully dried) of the coupled intermediate as a brown foam. Without purification this intermediate was used directly for the next reaction. ESI MS m/z (M+H)$^+$ 428.15.

The above coupled intermediate was dissolved in anhydrous toluene (6.5 L) and treated with HOAc (1.5 L, 26.23 mol, 6.5 equiv.). The mixture was heated at about 55° C. (bath temperature) for 3 hrs at which point the cyclization reaction was complete as indicated by HPLC. The reaction mixture was rotavapped and chased with toluene (5 L×2). The residue was dissolved in EtOAc (8 L) and washed with aq. NaHCO$_3$ (7.5 L). The aqueous layer was back-extracted with EtOAc (2 L) to recover small amount of the product. The combined organic solution was dried (Na$_2$SO$_4$) and rotavapped and vacuum dried to afford 1.98 kg (120% crude yield) of crude EP-019653 as a brown foam. HPLC purity was about 64% area). After multi-CombiFlash silica gel column chromatography purification (1.5 kg silica gel column×20) eluting with EtOAc and hexanes, about 1.0 kg of the title compound (~98% HPLC) was obtained from the above 1.98 kg of the crude product. ESI MS m/z (M+H)$^+$ 410.20.

Step 9: Synthesis of (S)-tert-butyl 6-(6-ethynyl-1H-benzo[d]imidazol-2-yl)-5-azaspiro[2.4]heptane-5-carboxylate

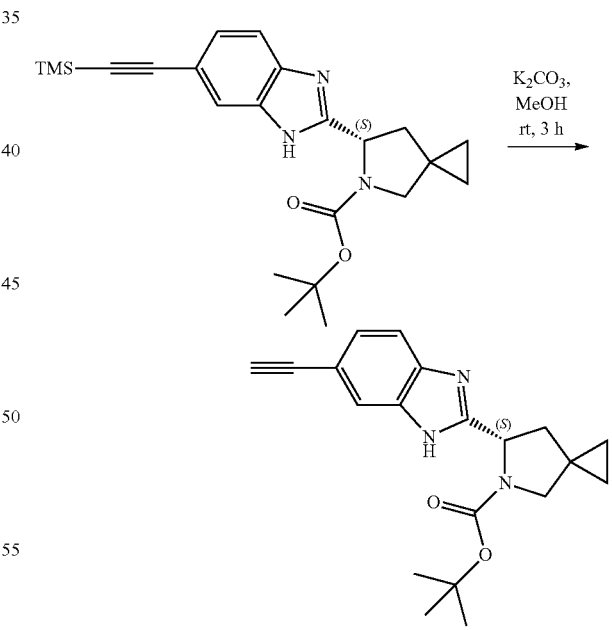

A brown opaque mixture of (S)-tert-butyl 6-(6-((trimethylsilyl)ethynyl)-1H-benzo[d]imidazol-2-yl)-5-azaspiro[2.4]heptane-5-carboxylate (0.99 kg, 2.41 mol, 1 equiv.) in methanol (5.5 L) is treated with solid potassium carbonate (340 g, 2.46 mol, 1.02 equiv.) for about 1.5 hours and the reaction was complete as indicated by TLC/MS. The mixture was rotavapped and solvent swapped to EtOAc (6 L), and then washed with 10% NaCl solution (5 L). Upon drying over Na₂SO₄ it was rotavapped and vacuum dried at about 25~30° C. overnight to afford 0.845 kg (104% yield, 98% HPLC purity) of the title compound as a light brown foam. ESI MS m/z (M+H)⁺ 338.19.

Step 10: Synthesis of 2-bromo-1-(4-iodophenyl)ethanone

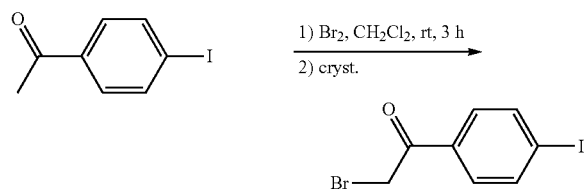

To a clear dark solution of 1-(4-iodophenyl)ethanone (1.046 kg, 4.251 mol, 1 equiv.) in DCM (8 L) was charged (dropwise) bromine (228 ml, 4.45 mol, 1.047 equiv.) over the period of 30 to 45 min at the ambient temperature. The reaction was slightly exothermic (temperature increased to about 20~25° C.) and released a lot of hydrogen bromide gas as the by-product. The reaction was considered as complete after 3 to 4 hrs as indicated by HPLC (typically ~7% starting material, ~10% di-bromo by-product, and ~83% desired mono-bromo product, all in area % by HPLC). It was then quenched and neutralized by aqueous NaHCO₃ solution wash (4 L), followed by brine wash (3 L). Upon drying over Na₂SO₄, it is rotavapped and solvent swapped to THF and the desired product was crystallized from THF (final volume about 2 L) at from 50° C. to 20° C. to afford the 1st crop: 340 g (98% HPLC purity); by concentrating the mother liquor to about half-volume to afford the 2nd crop: 426 g (98% HPLC purity); by further concentrating and addition of hexanes (i.e., THF/hexanes, 1:1) to afford the 3rd crop: 339 g (97+% HPLC purity). The combined crystal title compound was 1.105 kg (80% yield). ¹H NMR (500 MHz, CDCl₃): 7.88 (d, 2H), 7.70 (d, 2H), 4.42 (s, 2H).

Step 11: Synthesis of (S)-tert-butyl 6-(5-(4-iodophenyl)-1H-imidazol-2-yl)-5-azaspiro[2.4]heptane-5-carboxylate

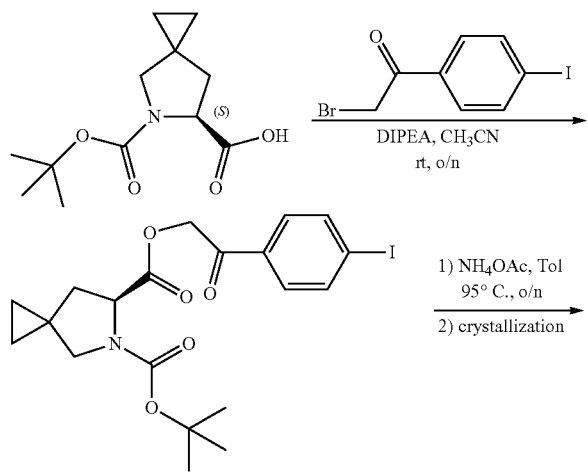

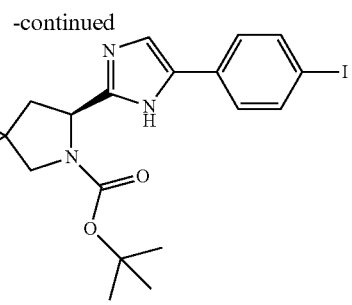

This was a 2-step reaction process. To a solution of (S)-5-(tert-butoxycarbonyl)-5-azaspiro[2.4]heptane-6-carboxylic acid (1.122 kg, 4.65 mol, 1 equiv.) in anhydrous MeCN (10 L) was charged 4'-iodo bromoacetophenone (1.56 kg, 4.80 mol, 1.032 equiv.). The resulting suspension was charged DIPEA (1.215 L, 1.5 equiv.) at the ambient temperature over the period of about 15 min. Upon the completion of the DIPEA addition, the reaction was slightly exothermic (the internal temperature increased up to 25° C.) and the reaction mass became a clear solution. The reaction was complete within a couple of hours as indicated by HPLC (99+% conversion). It was rotavapped down, solvent swapped to EtOAc (11 L), subsequently washed with water (3 L), then sodium bicarbonate solution (3 L), and finally with brine (2 L). Upon drying over Na₂SO₄, it was rotavapped to dryness and chased with toluene (4 L×2) to dryness and finally charged toluene (8 L) to give a solution of the coupled intermediate in toluene (about 86% HPLC purity). ESI MS m/z (M+H)⁺ 486.13.

Without isolation/purification, this toluene solution of the above intermediate was further treated with large excess amount of ammonium acetate (3.5 kg, 45.4 mol, 9.77 equiv.) and more toluene (1 L). The resulting suspension was slowly heated up to 95° C. over the period of about 1.5 hrs [CAUTION: gas evolution!] and held at 95 to 100° C. for additional 7 hrs at which point the reaction was complete as evidenced by HPLC (99% HPLC conversion). Upon cooling down, the reaction mixture was washed with aqueous saturated NaHCO₃ (3 L×3) and then with 15% NaCl (4 L). After drying over Na₂SO₄, it was filtered through a short pad of silica gel (about 0.7 g and 2 inch thick) and washed with toluene (2 L) and with EtOAc/hexanes (1:1) (8 L) to remove the TLC baseline impurities. The combined organic solution was rotavapped to dryness and chased with MeCN (2 L) to give the crude product in ~90% HPLC purity. This crude product was dissolved in MeCN (6.7 L) at about 50° C. as a clear solution, slowly cooled down and crystallized out. The slurry was agitated at about 16 to 20° C. for at least 1 hr before filtration and washing (chilled MeCN) to afford the title compound (1.188 kg after vacuum drying, 97.5% HPLC purity). The 2nd crop of the product was obtained by concentrating the above mother liquor and seeding/crystallizing at room temperature overnight to afford additional 260 g in 96% HPLC purity. The combined yield was 1.448 kg (67% yield for 2-step reaction process starting from (S)-5-(tert-butoxycarbonyl)-5-azaspiro[2.4]heptane-6-carboxylic acid). ESI MS m/z (M+H)⁺ 466.09.

Step 12: Synthesis of Bis-Boc Intermediate

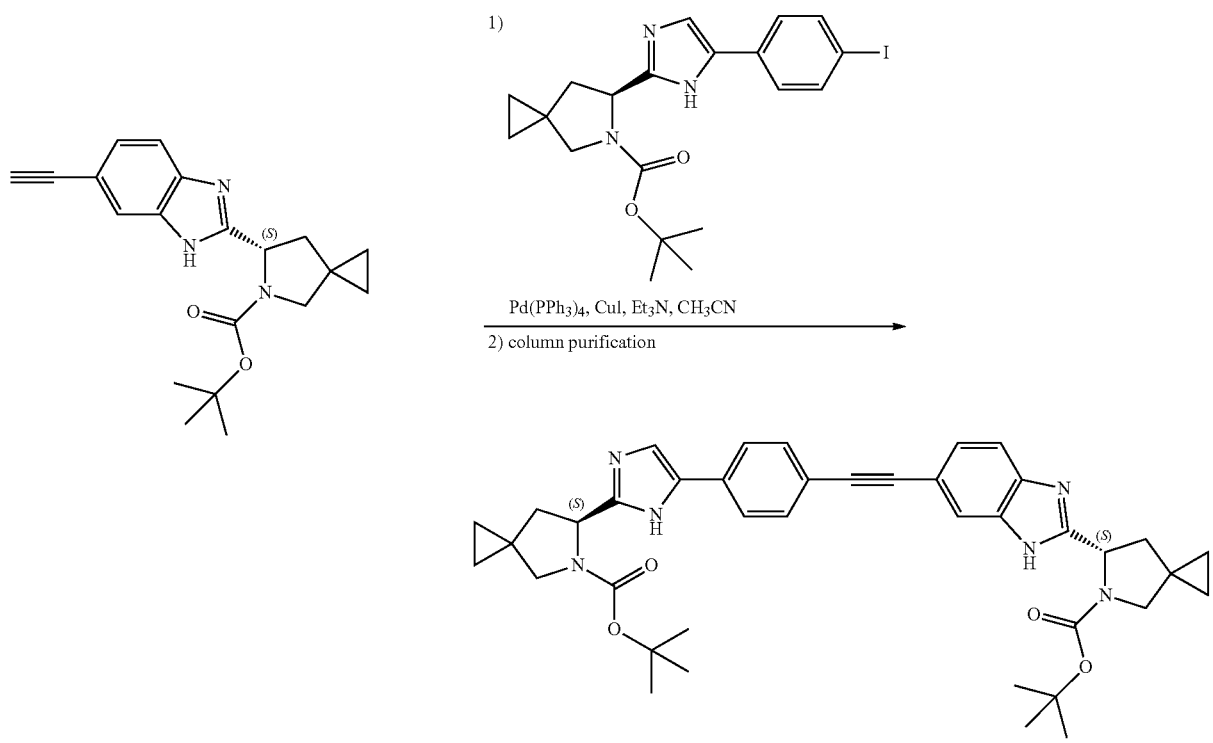

A mixture of alkyne (S)-tert-butyl 6-(6-ethynyl-1H-benzo[d]imidazol-2-yl)-5-azaspiro[2.4]heptane-5-carboxylate (0.845 kg, ~2.41 mol, 1 equiv.) and iodide (S)-tert-butyl 6-(5-(4-iodophenyl)-1H-imidazol-2-yl)-5-azaspiro[2.4]heptane-5-carboxylate (1.149 kg, 2.47 mol, 1.02 equiv.) in MeCN (4 L) and TEA (3 L, 21.49 mol, 8.9 equiv.) was degassed by $N_2$ gas bubbling (15 min) to give a brownish suspension. Under $N_2$, it was charged catalyst Pd(PPh$_3$)$_4$ (56 g, 0.0485 mol, 2 mol %) and followed by CuI (18.4 g, 0.0966 mol, 4 mol %). The resulting mixture was continued to degass as above for 5 min and then warmed up to about 40° C. (bath temperature). The reaction was complete within 3 hrs as evidenced by HPLC. It was evaporated and solvent swapped to EtOAc (16 L), washed with aqueous sodium bicarbonate solution (5 L). After drying over Na$_2$SO$_4$, it was rotavapped to dryness to afford a yellowish foam as the crude product in about 87% HPLC purity. The crude product was purified by multi-CombiFlash (1.5 kg silica gel column) chromatography eluting with EtOAc and hexanes to afford about 1.3 kg (80% yield from (S)-tert-butyl 6-(6-((trimethylsilyl)ethynyl)-1H-benzo[d]imidazol-2-yl)-5-azaspiro[2.4]heptane-5-carboxylate) of the title compound. ESI MS m/z (M+H)$^+$ 675.37.

Step 13: Synthesis of N-MOC-L-valine

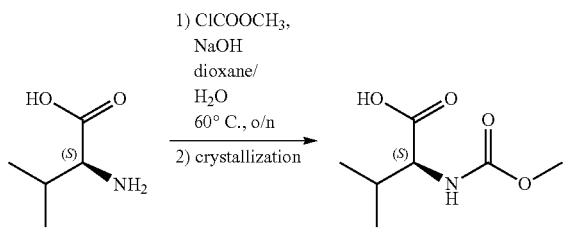

To a solution of solid NaOH (1.31 kg, 32.75 mol, 3.2 equiv.) in water (16.3 L) at about 25° C. was charged L-valine (1.2 kg, 10.243 mol, 1 equiv.) and agitated for 20 to 30 min to give a clear solution. It was further charged 1,4-dioxane (3.6 L) and cooled the resulting mixture with the jacket temperature at 15° C. Methyl chloroformate (1.575 L, 20.47 mol, 2 equiv.) was added dropwise over the period of about 30 min. The internal temperature was increased to about 45° C. during this exothermic addition and lots of gas evolved. Upon the completion of methyl chloroformate addition, the mixture was heated at about 60° C. overnight (18 hrs) at which point the reaction was complete. After cooling down, It was extracted with DCM (6 L×2) and discarded. The aqueous solution was then acidified at below 20° C. with concentrated HCl (about 1.1 L) to pH 1 to 2 to afford a white suspension. The suspension mixture was extracted with EtOAc (8 L×2). Upon drying over Na$_2$SO$_4$, it was rotavapped to dryness to leave a white solid. Then it was charged EtOAc (3 L) and warmed to abour 60° C. to give a clear solution. Hexanes (about 4.5 L) was slowly charged into the above EtOAc solution while maintaining the temperature about 50° C. to 60° C. Upon the completion of hexanes addition, crystallization occurred soon. The white slurry was agitated at 15 to 20° C. for at least 2 hrs before filtration, washing (EtOAc/Hexanes, 1:4), and vacuum drying at 30° C. overnight to afford 0.975 kg (98+% by NMR, no D-isomer detected by HPLC through its derivative). The 2nd crop was obtained by concentrating the mother liquor and crystallized from EtOAc/Hexanes (1:1) to afford additional 0.36 kg (same quality as the 1st crop: 98+% by NMR, no D-isomer detected by HPLC through its derivative). The combined yield was 1.335 kg (74.6% yield). ESI MS m/z (M+H)$^+$ 176.14.

Step 14: Synthesis of HCl salt of De-Boc Intermediate

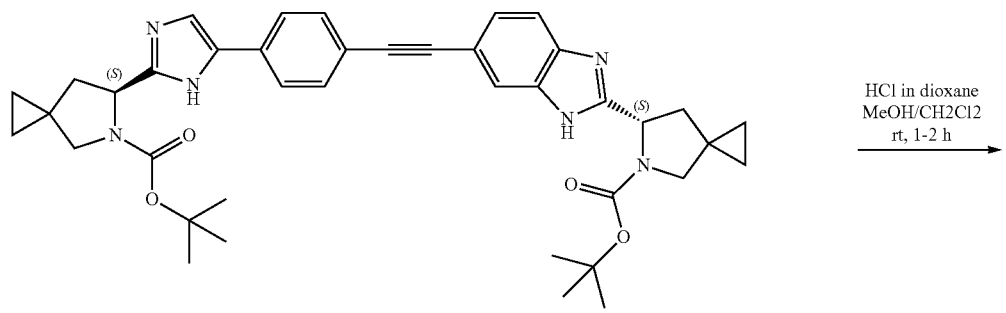

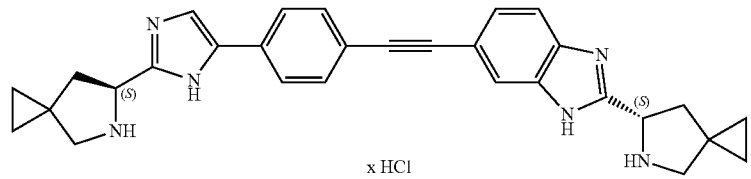

To a solution of bis-Boc intermediate from step 12 (910 g, 97.7% HPLC, 1.348 mol, 1 equiv.) in a mixture of DCM (6.4 L) and MeOH (0.45 L) at the ambient temperature was charged via a dropping funnel 4N HCl (g) in dioxane solution (3.6 L, ~10.7 equiv.) over the period of about 20 to 30 min. A lot of gas evolution was observed and the internal temperature was increased up to 33° C. The resulting slurry was agitated at room temperature for 60 min at which point the reaction was complete as evidenced by HPLC. It was filtered and cake washed with DCM (2 L), then air-dried overnight to afford 848 g (~100% yield) of the title compound as an off-white to light yellow dry powder. Checked $^1$HNMR (98+% purity). ESI MS m/z (M+H)$^+$ 475.23.

Step 15: Synthesis of (S)-2-Methoxycarbonylamino-1-((S)-6-(5-(4-((2-((S)-5-((S)-2-methoxycarbony-lamino-3-methylbutanoyl)-5-azaspiro[2.4]heptan-6-yl)-1H-benzo[d]imidazol-6-yl)ethynyl)phenyl)-1H-imidazol-2-yl)-5-azaspiro[2.4]heptan-5-yl)-3-methylbutan-1-one

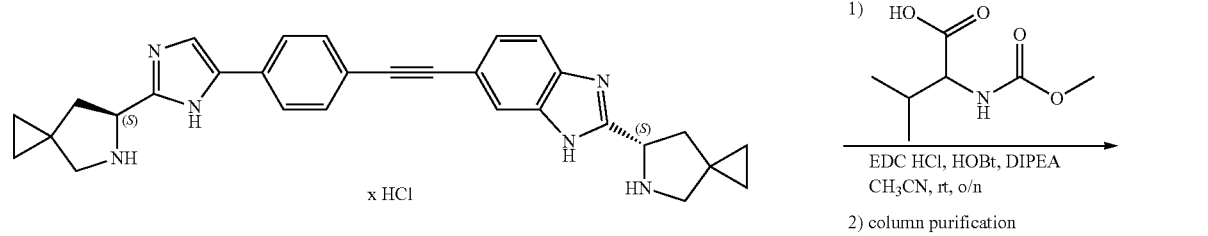

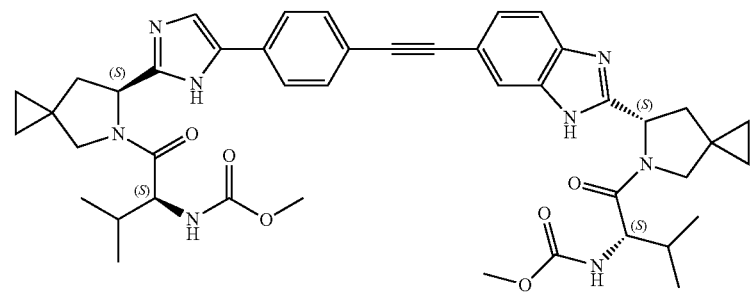

To a suspension of N-MOC-L-valine (519 g, 2.963 mol, 2.2 equiv.) and HOBT hydrate (455 g, 3.367 mol, 2.5 equiv.) in anhydrous MeCN (7.3 L) was charged EDC hydrochloride (620 g, 3.234 mol, 2.4 equiv.). The internal temperature was increased to about 20° C. from 13° C. The resulting clear solution was agitated at about 20° C. for 50 minutes. It was then charged with the product obtained from step 14 (848 g) followed by anhydrous MeCN (1.8 L). Upon cooling this resulting suspension to about 0~5° C., it was added via a dropping funnel DIPEA (1.5 L, 8.611 mol, ~6.4 equiv.) to pH 8 to 8.5 over the period of 40 to 60 min. The internal temperature was controlled at below 10° C. during the DIPEA addition. The reaction mixture became an almost clear solution after the DIPEA addition. The cooling bath was removed and it was agitated at about 20° C. overnight (18 hrs) at which point the reaction was complete as evidenced by HPLC (99+% conversion). The reaction was quenched by charging 15% aqueous NaCl solution (3.6 L) and agitated for 30 min. Then it was charged with iPAC (12 L). Upon separation, the aqueous layer was back-extracted with iPAC (2 L) to recover small amount of the product. The combined organic solution was washed twice with a mixture of 0.5N NaOH (4.5 L) and brine (1.8 L) followed by brine wash twice (3.6 L×2). After drying over $Na_2SO_4$, it was rotavapped and vacuum dried at 30° C. for 24 hrs to afford 1.13 kg amorphous solid. The crude HPLC purity was 95.3%.

The crude product was purified by multi-CombiFlash (1.5 kg silica gel column) chromatography eluting with 0.8% to 4% MeOH in EtOAc to afford 852 g of the title compound. The purity was 98% by HPLC area. The yield was ~80% for the 2-step process starting from bis-Boc intermediate from step 12. ESI MS m/z $(M+H)^+$ 789.41.

While this invention has been particularly shown and described with references to preferred embodiments thereof, it will be understood by those skilled in the art that various changes in form and details may be made therein without departing from the scope of the invention encompassed by the appended claims.

What is claimed:
1. A process for the preparation of compounds of Formula (I):

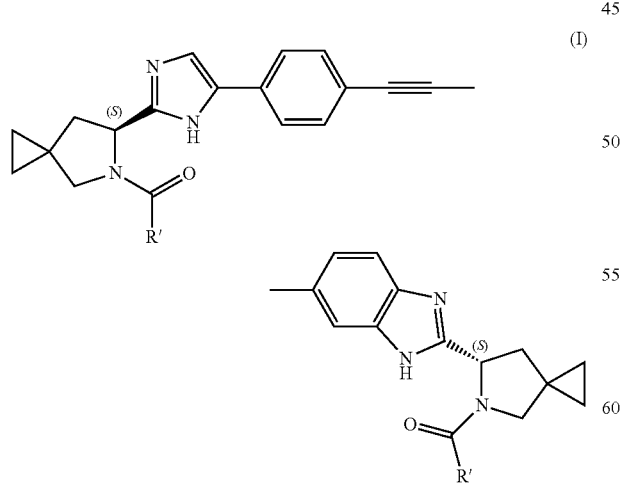

wherein each R' is independently selected from substituted $C_1$-$C_8$ alkyl groups or a pharmaceutically acceptable salt thereof;

said process comprising the steps of:
(a) providing a compound of Formula (III):

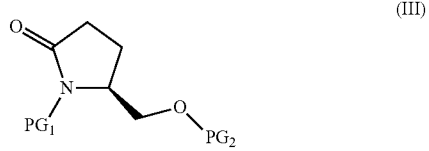

wherein $PG_1$ is selected from the group consisting of —C(O)—R, —C(O)—OR, —S(O)$_2$—R, —C(O)N(R)$_2$, and —S(O)$_2$N(R)$_2$;
each R is independently selected from the group consisting of hydrogen, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkenyl, heterocyclic, aryl, and heteroaryl, each optionally substituted;
$PG_2$ is selected from acyl, silyl, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, and a saturated or unsaturated heterocyclic group;
alternatively, $PG_1$ and $PG_2$ are tethered together to form a heterocyclic ring;
(b) treating the compound of Formula (III) with a deprotonating agent followed by an alkylating agent followed by quaternizing agent to provide a compound of Formula (IV):

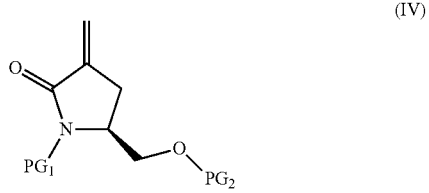

(c) reacting the compound of Formula (IV) with a sulfur ylide in the presence of a base to yield a compound of Formula (V):

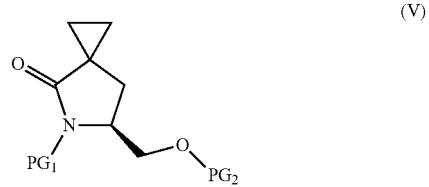

(d) reducing and deprotecting the compound of Formula (V) to provide a compound of Formula (VI):

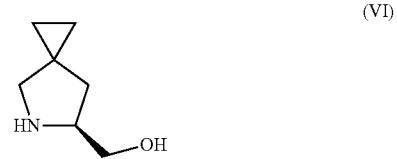

(e) protecting the compound of Formula (VI) to yield a compound of Formula (VII):

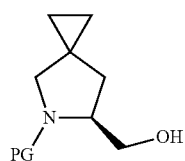

(VII)

wherein PG is selected from the group consisting of —R, —C(O)—R, —C(O)—OR, —S(O)₂—R, —C(O)N(R)₂, and —S(O)₂N(R)₂, wherein R is as previously defined;

(f) reacting the compound of Formula (VII) with an oxidizing reagent to yield a compound of Formula (VIII):

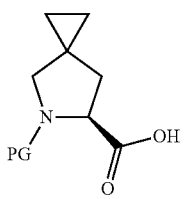

(VIII)

(g) reacting the compound of Formula (IX):

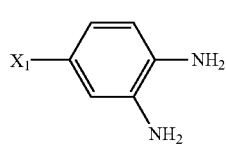

(IX)

wherein $X_1$ is a leaving group,
with $R_1$—≡—H, wherein $R_1$ is hydrogen or silyl, in the presence of a metallic catalyst or a combination of metallic catalysts to provide a compound of Formula (X):

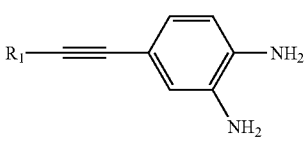

(X)

(h) reacting the compound of Formula (VIII) with the compound of Formula (X) under amide formation condition to provide a mixture of compounds of Formulae (XI-a) and (XI-b):

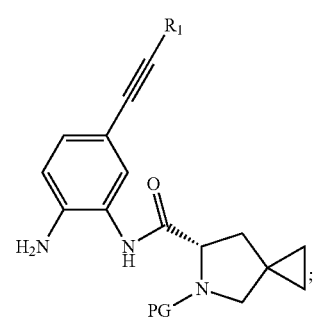

(XI-a)

(XI-b)

(i) treating the mixture of compounds of Formulae (XI-a) and (XI-b) with an acid to yield a compound of Formula (XII):

(XII)

(j) optionally when $R_1$ is a silyl group, treating the compound of Formula (XII) with a base to yield a compound of Formula (XII-a):

(XII-a)

(k) treating the compound of Formula (XIII)

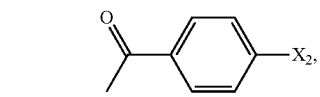

wherein $X_2$ is a leaving group, with a halogenating reagent to yield a compound of Formula (XIV):

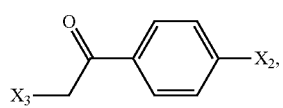

(XIV)

wherein $X_3$ is halogen;

(l) reacting the compound of Formula (VIII) with the compound of Formula (XIV) in the presence of an base to provide a compound of Formula (XV):

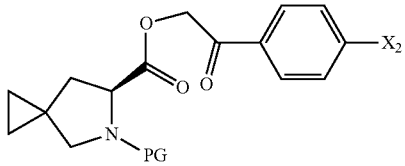

(XV)

(m) treating the compound of formula (XV) with an ammonium salt to provide a compound of Formula (XVI):

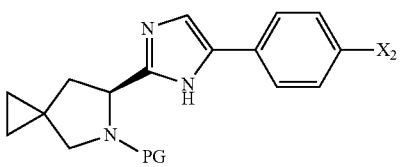

(XVI)

(n) reacting the compound of Formula (XII-a) with the compound of Formula (XVI) in the presence of a metallic catalyst to provide a compound of Formula (XVII):

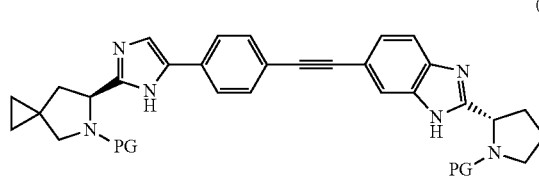

(XVII)

(o) deprotecting the compound of Formula (XVII) to provide a compound of Formula (XVIII):

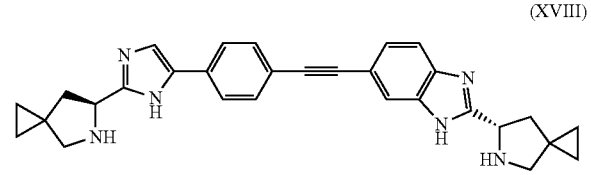 [SMILES: C(#Cc1ccc2nc([C@@H]3CC4(CC4)CN3)[nH]c2c1)c1ccc(-c2cnc([C@@H]3CC4(CC4)CN3)[nH]2)cc1]

(XVIII)

(p) reacting the compound of Formula (XVIII) with

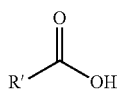

under amide formation condition to provide a compound of Formula (I):

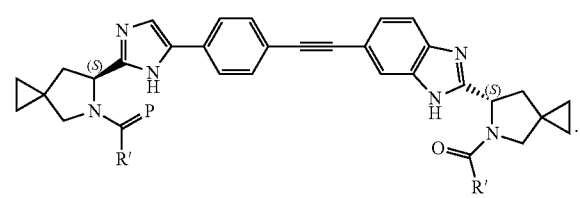

(I)

2. The process of claim 1, wherein for formulae (III), (IV) and (V), $PG_1$ and $PG_2$ are tethered together to form compounds of formulae (III-a), (IV-a) and (V-a):

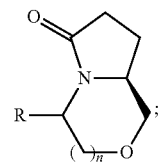

(III-a)

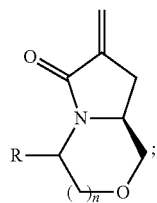

(IV-a)

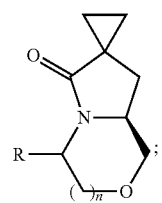

(V-a)

wherein R is as previously defined and n is 0, 1, or 2.

3. The process of claim 2, wherein n is 0 and R is hydrogen, optionally substituted alkyl or optionally substituted aryl.

4. The process of claim 1, wherein PG is Boc or Cbz; $R_1$ is hydrogen, trimethylsilyl or triethylsilyl; $X_1$, $X_2$ or $X_3$ is respectfully iodine or bromine; and R' is $C_1$-$C_8$ alkyl substituted with —$NHCO_2$($C_1$-$C_4$ alkyl) or —O($C_1$-$C_4$ alkyl); or a pharmaceutically acceptable salt thereof.

5. The process of claim 1, wherein for step (b), the deprotonating agent is LiHMDS, NaHMDS, nBuLi or LDA; the alkylating agent is Eschenmoser's salt; and the quaternizing agent is methyl iodide.

6. The process of claim 1, wherein for step (c), the sulfur glide is trimethylsulfoxonium iodide; the base is sodium hydride or potassium tert-butoxide; and in the presence of a solvent selected from the group consisting of THF, DMF and DMSO.

7. The process of claim 1, wherein for step (d), the reducing reagent is lithium aluminum hydride; the deprotection is achieved by transfer hydrogenation, in the presence of a metal catalyst which is palladium (0); and a hydrogen source wherein the hydrogen source is ammonium formate.

8. The process of claim 1, wherein for step (f), the oxidizing agents are selected from chromium(VI) reagent, $RuCl_3$/$NaIO_4$, potassium permanganate, or sodium chlorite.

9. The process of claim 1, wherein for steps (g) or (n), the metallic catalysts are CuI and Pd(PPh$_3$)$_4$; in the presence of a base which is triethylamine or diisopropylethylamine; and a solvent which is acetonitrile, THF or DMF.

10. The process of claim 1, wherein for steps (h) or (p), the amide formation is achieved by using reagents EDC.HCl, HATU or their combination.

11. The process of claim 1, wherein for step (i), the acid is acetic acid.

12. The process of claim 1, wherein for step (j), the base is potassium carbonate or cesium carbonate; and in the presence of a solvent which is methanol or ethanol.

13. The process of claim 1, wherein for step (l), the base is triethylamine or diisopropylethylamine; and in the presence of a solvent which is acetonitrile, THF or DMF.

14. The process of claim 1, wherein for step (m), the ammonium salt used is ammonium acetate, ammonium formate or ammonium carbonate.

15. The process of claim 1, wherein for step (o), the deprotecting agent is an acid such as hydrochloric acid.

* * * * *

UNITED STATES PATENT AND TRADEMARK OFFICE
CERTIFICATE OF CORRECTION

PATENT NO.        : 8,921,573 B2                                              Page 1 of 1
APPLICATION NO.   : 14/253976
DATED             : December 30, 2014
INVENTOR(S)       : Datong Tang et al.

It is certified that error appears in the above-identified patent and that said Letters Patent is hereby corrected as shown below:

In the Claims

At Column 43

In claim 1, at lines 57-64, should read,

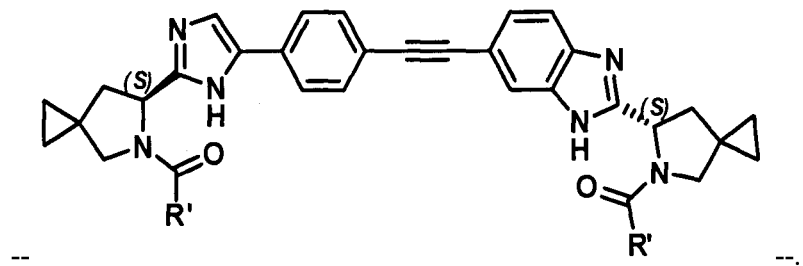

--                                                          --.

At Column 44

In claim 6, at line 47, delete "glide" and insert -- ylide --.

Signed and Sealed this
Ninth Day of June, 2015

Michelle K. Lee
*Director of the United States Patent and Trademark Office*